US010709504B2

(12) United States Patent
Scheller et al.

(10) Patent No.: US 10,709,504 B2
(45) Date of Patent: Jul. 14, 2020

(54) CURVED LASER PROBE WITH SINGLE-USE OPTIC FIBER

(71) Applicant: Katalyst Surgical, LLC, Chesterfield, MO (US)

(72) Inventors: Gregg D Scheller, Wildwood, MO (US); Matthew N Yates, High Ridge, MO (US); Steven G Scheller, Chesterfield, MO (US); Daniel J Wiener, St. Charles, MO (US)

(73) Assignee: KATALYST SURGICAL, LLC, Chesterfield, MO (US)

( * ) Notice: Subject to any disclaimer, the term of this patent is extended or adjusted under 35 U.S.C. 154(b) by 73 days.

(21) Appl. No.: 15/677,303

(22) Filed: Aug. 15, 2017

(65) Prior Publication Data

US 2018/0078311 A1 Mar. 22, 2018

Related U.S. Application Data

(60) Provisional application No. 62/396,594, filed on Sep. 19, 2016.

(51) Int. Cl.
*A61B 18/00* (2006.01)
*A61B 18/24* (2006.01)
(Continued)

(52) U.S. Cl.
CPC ............ *A61B 18/24* (2013.01); *A61B 18/22* (2013.01); *A61F 9/00821* (2013.01);
(Continued)

(58) Field of Classification Search
CPC ........... A61B 2018/00172; A61B 2018/00321; A61B 2018/00404; A61B 2018/0041;
(Continued)

(56) References Cited

U.S. PATENT DOCUMENTS 3,174,851 A 3/1965 Buehler et al.
4,122,853 A 10/1978 Smith
(Continued)

FOREIGN PATENT DOCUMENTS

EP    EP 0900547 B1    3/1999
GB    2208805 A    4/1989
(Continued)

OTHER PUBLICATIONS

H. Fischer, B. Vogel, W. Pfleging, H. Besser, Flexible distal tip made of nitinol (NiTi) for a steerable endoscopic camera system, Materials Science and Engineering A273-275 (1999) 780-783.
(Continued)

*Primary Examiner* — Eugene T Wu

(57) ABSTRACT

A curved laser probe with single-use optic fiber may include a reusable handle, an optic fiber fixture, and a single-use optic fiber. The single-use optic fiber may include an optic fiber having an optic fiber distal end and an optic fiber proximal end. The optic fiber may be disposed in a first transitory connector having a first transitory connector distal end and a first transitory connector proximal end wherein the optic fiber distal end extends a fixed distance from the transitory connector distal end. The optic fiber may be disposed in a second transitory connector having a second transitory connector distal end and a second transitory connector proximal end wherein the optic fiber proximal end extends a fixed distance from the second transitory connector distal end. The first transitory connector may be inserted in the reusable handle and the second transitory connector may be inserted in the optic fiber fixture.

18 Claims, 11 Drawing Sheets

(51) Int. Cl.
*A61F 9/008* (2006.01)
*A61B 18/22* (2006.01)
*A61B 18/20* (2006.01)
*A61B 17/00* (2006.01)

(52) U.S. Cl.
CPC ............ *A61F 9/00823* (2013.01); *A61B 2017/00845* (2013.01); *A61B 2017/00853* (2013.01); *A61B 2017/00955* (2013.01); *A61B 2018/00029* (2013.01); *A61B 2018/00172* (2013.01); *A61B 2018/00178* (2013.01); *A61B 2018/00589* (2013.01); *A61B 2018/2005* (2013.01); *A61B 2018/2211* (2013.01); *A61B 2018/2222* (2013.01); *A61F 2009/00863* (2013.01)

(58) Field of Classification Search
CPC .......... A61B 2018/00416; A61B 2018/00422; A61B 2018/00428; A61B 2018/00595; A61B 2018/0091; A61B 2018/00964; A61B 2018/0097; A61B 2018/2005; A61B 2018/2015; A61B 2018/2205; A61B 2018/2244; A61B 2018/225; A61B 2018/2253; A61B 2018/2285; A61B 2018/2288; A61B 18/20; A61B 18/22; A61B 18/24; A61F 9/007; A61F 9/008; A61F 9/00821; A61F 9/00823
See application file for complete search history.

(56) References Cited

U.S. PATENT DOCUMENTS

| | | | |
|---|---|---|---|
| 4,147,443 A | 4/1979 | Skobel | |
| 4,687,293 A | 8/1987 | Randazzo | |
| 4,744,360 A | 5/1988 | Bath | |
| 4,870,952 A | 10/1989 | Martinez | |
| 5,190,050 A | 3/1993 | Nitzsche | |
| 5,228,852 A | 7/1993 | Goldsmith et al. | |
| 5,257,988 A | 11/1993 | L'Esperance, Jr. | |
| 5,322,055 A | 6/1994 | Davison et al. | |
| 5,322,064 A | 6/1994 | Lundquist | |
| 5,346,504 A | 9/1994 | Ortiz et al. | |
| 5,355,871 A | 10/1994 | Hurley et al. | |
| 5,381,782 A | 1/1995 | DeLaRama et al. | |
| 5,439,000 A | 8/1995 | Gunderson et al. | |
| 5,454,794 A | 10/1995 | Narciso et al. | |
| 5,520,222 A | 5/1996 | Chikama | |
| 5,735,842 A | 4/1998 | Kruege et al. | |
| 5,855,577 A | 1/1999 | Murphy-Chutorian et al. | |
| 5,873,865 A | 2/1999 | Horzewski et al. | |
| 5,951,544 A | 9/1999 | Konwitz | |
| 6,123,699 A | 9/2000 | Webster, Jr. | |
| 6,126,654 A | 10/2000 | Giba et al. | |
| 6,178,354 B1 | 1/2001 | Gibson | |
| 6,198,974 B1 | 3/2001 | Webster, Jr. | |
| 6,330,837 B1 | 12/2001 | Charles et al. | |
| 6,352,531 B1 | 3/2002 | O'Connor et al. | |
| 6,488,695 B1 | 12/2002 | Hickingbotham | |
| 6,505,530 B2 | 1/2003 | Adler et al. | |
| 6,530,913 B1 | 3/2003 | Giba et al. | |
| 6,533,772 B1 | 3/2003 | Sheds et al. | |
| 6,551,302 B1 | 4/2003 | Rosinko et al. | |
| 6,554,794 B1 | 4/2003 | Mueller et al. | |
| 6,572,608 B1 | 6/2003 | Lee et al. | |
| 6,620,153 B2 | 9/2003 | Mueller et al. | |
| 6,718,211 B2 * | 4/2004 | Smits ................... | A61N 1/056 607/122 |
| 6,730,076 B2 | 5/2004 | Hickingbotham | |
| 6,863,668 B2 | 3/2005 | Gillespie et al. | |
| 6,872,214 B2 | 3/2005 | Sonnenschein et al. | |
| 6,984,230 B2 | 1/2006 | Scheller et al. | |
| 7,004,957 B1 | 2/2006 | Dampney et al. | |
| 7,226,444 B1 | 6/2007 | Ellman et al. | |
| 7,303,533 B2 | 12/2007 | Johansen et al. | |
| 7,402,158 B2 | 7/2008 | Scheller et al. | |
| 7,555,327 B2 | 6/2009 | Matlock | |
| 7,632,242 B2 | 12/2009 | Griffin et al. | |
| 7,766,904 B2 | 10/2010 | Mc Gowan, Sr. et al. | |
| 7,935,108 B2 | 5/2011 | Baxter et al. | |
| 8,038,692 B2 | 10/2011 | Valencia et al. | |
| 8,075,553 B2 | 12/2011 | Scheller et al. | |
| 8,197,468 B2 | 6/2012 | Scheller et al. | |
| 8,840,605 B2 | 9/2014 | Scheller et al. | |
| 8,840,607 B2 | 9/2014 | Scheller et al. | |
| 8,968,277 B2 | 1/2015 | Scheller et al. | |
| 8,951,245 B2 | 2/2015 | Scheller et al. | |
| 9,023,019 B2 | 5/2015 | Scheller et al. | |
| 9,023,020 B2 | 5/2015 | Scheller et al. | |
| 9,039,686 B2 | 5/2015 | Scheller et al. | |
| 9,089,399 B2 | 7/2015 | Scheller et al. | |
| 9,107,682 B2 | 8/2015 | Scheller et al. | |
| 9,113,995 B2 | 8/2015 | Scheller et al. | |
| 9,119,702 B2 | 9/2015 | Scheller et al. | |
| 2001/0026666 A1* | 10/2001 | Ferrera .................. | G02B 6/403 385/123 |
| 2003/0171762 A1 | 9/2003 | Forchette et al. | |
| 2004/0181138 A1 | 9/2004 | Hindricks et al. | |
| 2004/0249367 A1 | 12/2004 | Saadat et al. | |
| 2005/0054900 A1 | 3/2005 | Mawn et al. | |
| 2005/0131399 A1 | 6/2005 | Loeb et al. | |
| 2005/0154379 A1 | 7/2005 | McGowen, Sr. et al. | |
| 2005/0157985 A1 | 7/2005 | McGowan, Sr. et al. | |
| 2005/0234437 A1 | 10/2005 | Baxter et al. | |
| 2005/0272975 A1 | 12/2005 | McWeeny et al. | |
| 2005/0277874 A1 | 12/2005 | Selkee | |
| 2006/0129175 A1 | 6/2006 | Griffen et al. | |
| 2006/0178674 A1 | 8/2006 | McIntyre | |
| 2006/0293270 A1 | 12/2006 | Adamis et al. | |
| 2007/0179475 A1 | 8/2007 | Scheller | |
| 2007/0185514 A1 | 8/2007 | Kirchhevel | |
| 2007/0260231 A1 | 11/2007 | Rose et al. | |
| 2008/0132761 A1 | 6/2008 | Sonnenschein et al. | |
| 2008/0208105 A1 | 8/2008 | Zelickson et al. | |
| 2008/0287938 A1 | 11/2008 | Scheller et al. | |
| 2009/0018993 A1 | 1/2009 | Dick et al. | |
| 2009/0163943 A1 | 6/2009 | Cavanaugh et al. | |
| 2009/0187170 A1 | 7/2009 | Auld et al. | |
| 2009/0312750 A1 | 12/2009 | Spaide | |
| 2010/0004642 A1 | 1/2010 | Lumpkin | |
| 2010/0191224 A1 | 7/2010 | Butcher | |
| 2010/0268234 A1 | 10/2010 | Aho et al. | |
| 2010/0331883 A1 | 12/2010 | Schmitz et al. | |
| 2011/0028947 A1 | 2/2011 | Scheller et al. | |
| 2011/0144627 A1 | 6/2011 | Smith | |
| 2011/0144630 A1 | 6/2011 | Loeb | |
| 2011/0190749 A1 | 8/2011 | McMillian et al. | |
| 2011/0280653 A1 | 11/2011 | Sjostedt et al. | |
| 2012/0116361 A1 | 5/2012 | Hanlon et al. | |
| 2012/0172656 A1* | 7/2012 | Walters ............... | A61M 1/1013 600/16 |
| 2012/0245569 A1 | 9/2012 | Papac et al. | |
| 2013/0035551 A1 | 2/2013 | Yu et al. | |
| 2013/0060240 A1 | 3/2013 | Scheller et al. | |
| 2013/0071507 A1 | 3/2013 | Scheller et al. | |
| 2013/0090635 A1 | 4/2013 | Mansour | |
| 2013/0096541 A1 | 4/2013 | Scheller et al. | |
| 2013/0116671 A1 | 5/2013 | Scheller et al. | |
| 2013/0144278 A1 | 6/2013 | Papac et al. | |
| 2013/0150838 A1 | 6/2013 | Scheller et al. | |
| 2013/0165910 A1 | 6/2013 | Scheller et al. | |
| 2013/0261610 A1 | 10/2013 | LaConte et al. | |
| 2013/0281994 A1 | 10/2013 | Scheller et al. | |
| 2013/0304043 A1 | 11/2013 | Scheller et al. | |
| 2013/0304048 A1 | 11/2013 | Scheller et al. | |
| 2014/0005642 A1 | 1/2014 | Scheller et al. | |
| 2014/0039471 A1 | 2/2014 | Scheller et al. | |
| 2014/0039472 A1 | 2/2014 | Scheller et al. | |
| 2014/0039475 A1 | 2/2014 | Scheller et al. | |
| 2014/0046307 A1 | 2/2014 | Scheller et al. | |
| 2014/0052115 A1 | 2/2014 | Zeid et al. | |
| 2014/0066907 A1 | 3/2014 | Scheller et al. | |
| 2014/0066912 A1 | 3/2014 | Scheller et al. | |
| 2014/0074073 A1 | 3/2014 | Scheller et al. | |

(56) References Cited

U.S. PATENT DOCUMENTS

| | | |
|---|---|---|
| 2014/0074079 A1 | 3/2014 | Scheller et al. |
| 2014/0088572 A1 | 3/2014 | Scheller et al. |
| 2014/0088576 A1 | 3/2014 | Scheller et al. |
| 2014/0107628 A1 | 4/2014 | Scheller et al. |
| 2014/0107629 A1 | 4/2014 | Scheller et al. |
| 2015/0038950 A1* | 2/2015 | Scheller .............. A61F 9/00821 606/4 |
| 2017/0135859 A1* | 5/2017 | Scheller ................ A61B 90/30 |
| 2017/0281411 A1* | 10/2017 | Scheller .............. A61F 9/00821 |
| 2018/0000645 A1* | 1/2018 | Scheller ............... G02B 6/4243 |
| 2018/0021088 A1* | 1/2018 | Scheller ................ A61B 18/22 606/4 |

FOREIGN PATENT DOCUMENTS

| | | |
|---|---|---|
| WO | WO 2011/019581 A1 | 2/2001 |
| WO | WO 2006/091597 A1 | 8/2006 |
| WO | WO 2007/038433 A2 | 4/2007 |
| WO | WO 2013/133717 | 9/2013 |

OTHER PUBLICATIONS

Ferry P.W. Melchels, Jan Feijen, Dirk W. Grijpma, A review on stereolithography and its applications in biomedical engineering, Biomaterials 31 (2010) 6121-6130.

\* cited by examiner

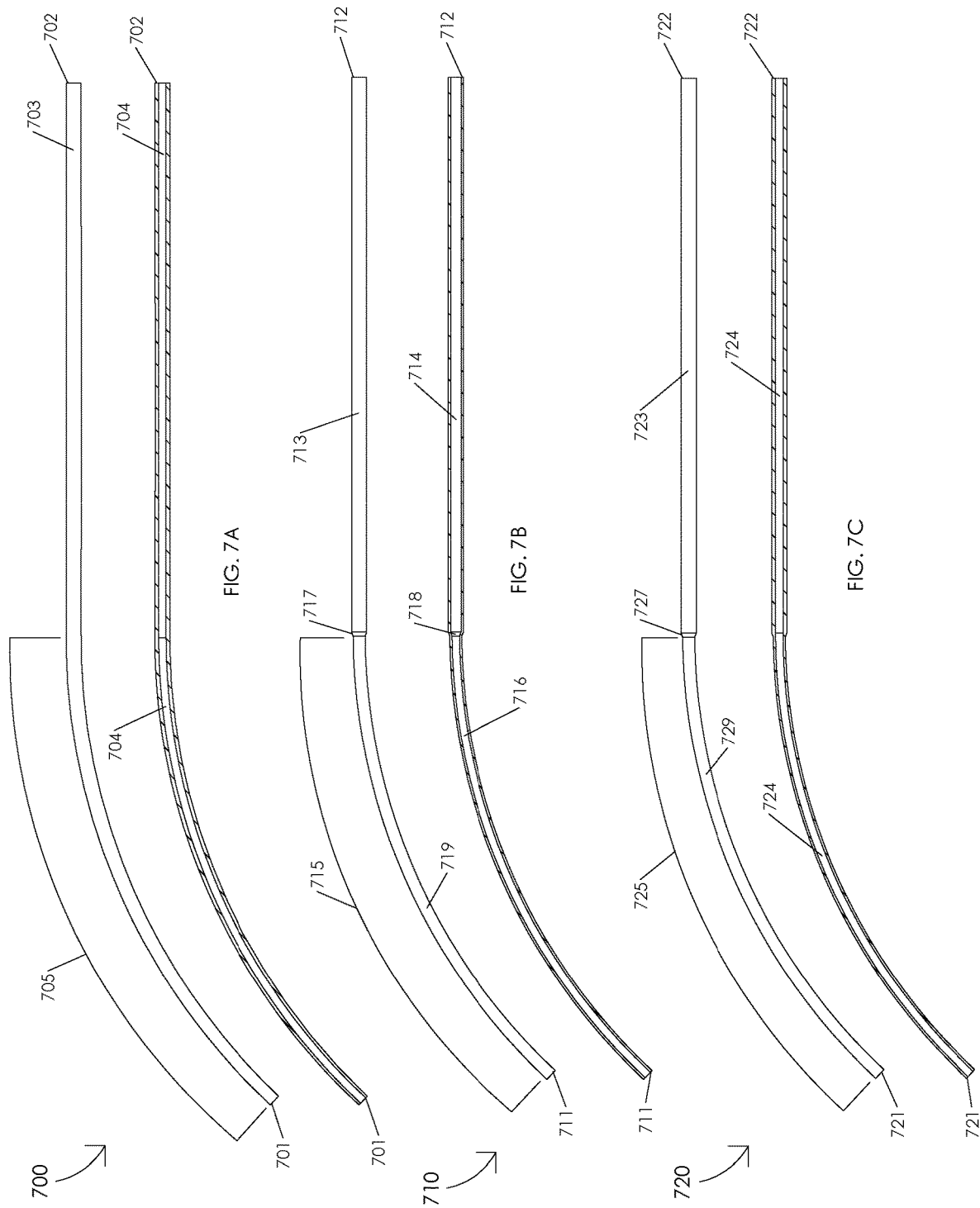

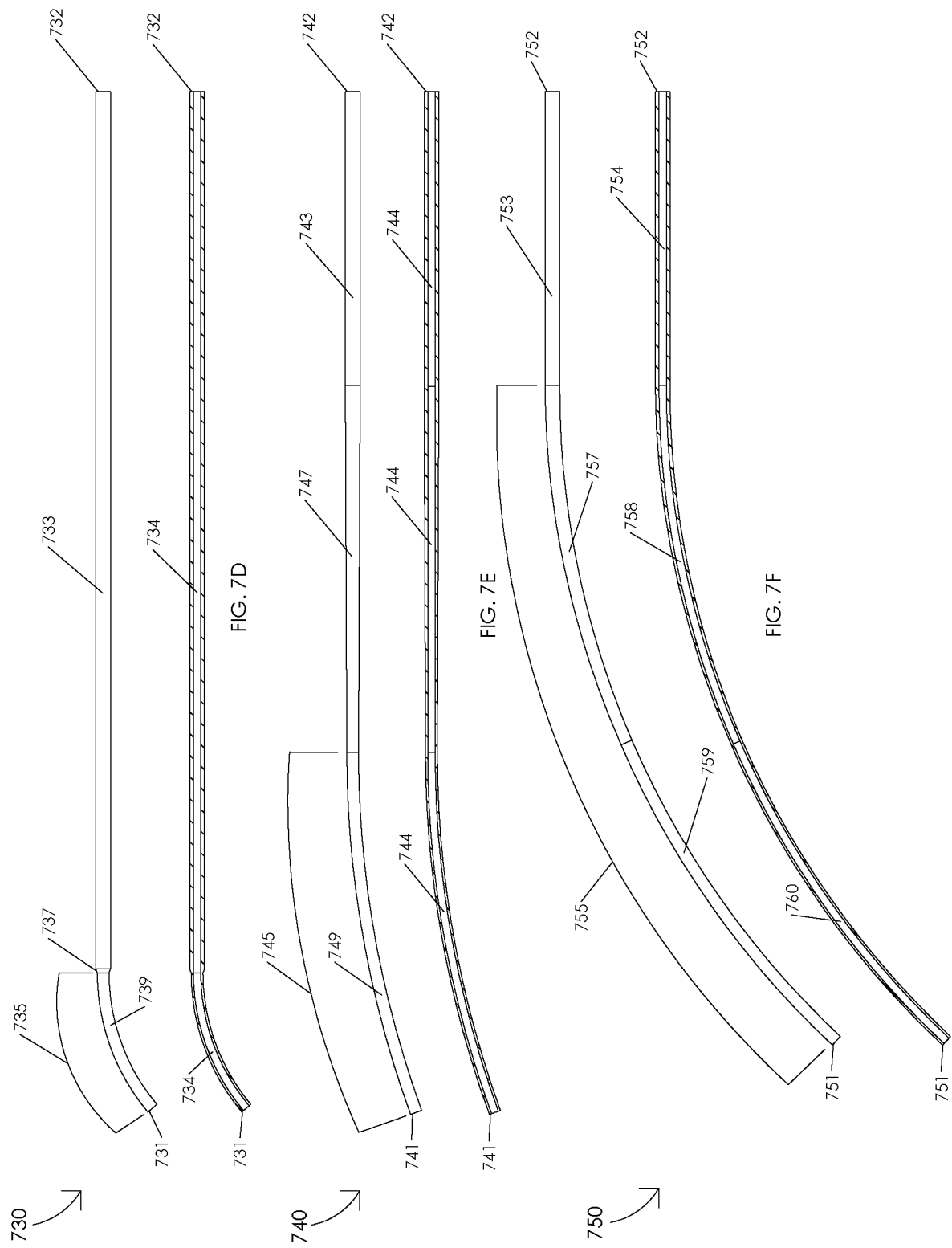

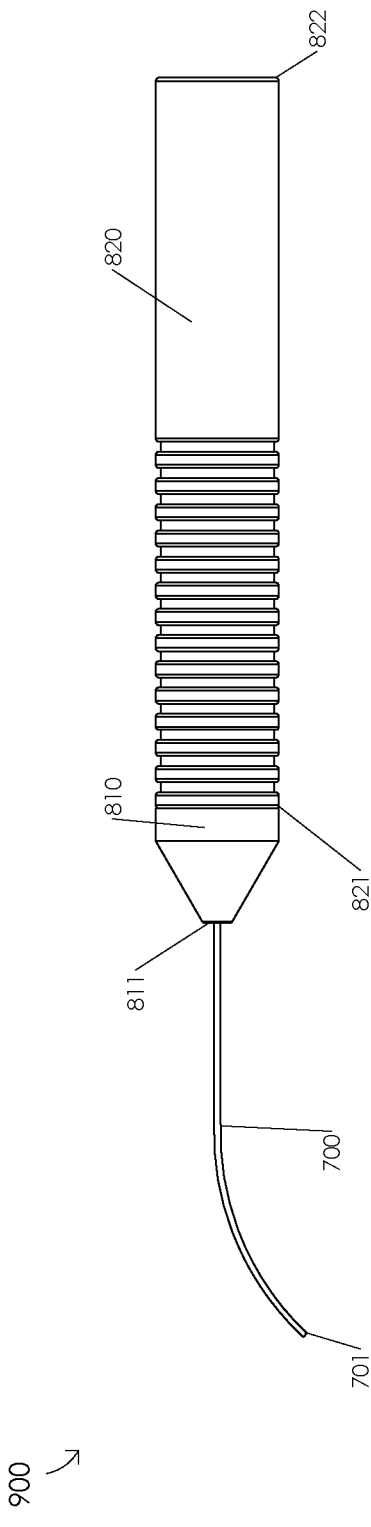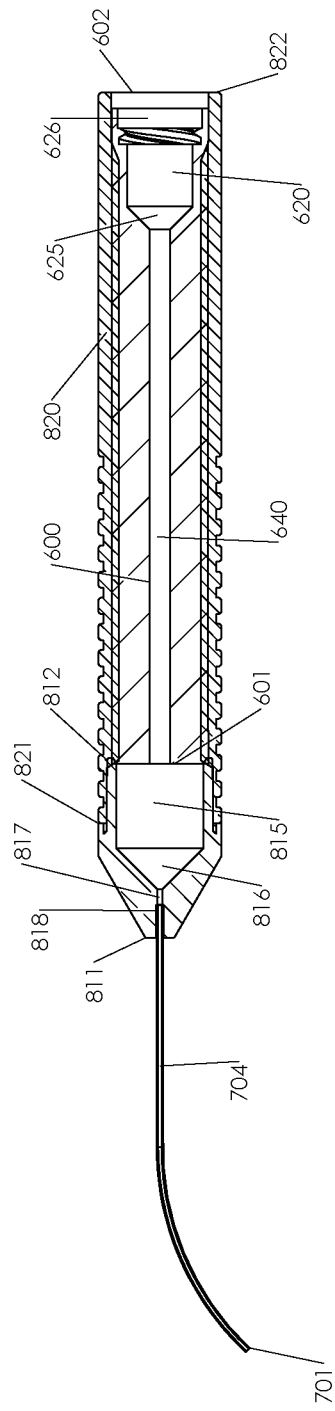
FIG. 9A
FIG. 9B

CURVED LASER PROBE WITH SINGLE-USE OPTIC FIBER

CROSS-REFERENCE TO RELATED APPLICATIONS

This Application claims the benefit of U.S. Provisional Application No. 62/396,594, filed Sep. 19, 2016.

FIELD OF THE INVENTION

The present disclosure relates to a surgical instrument, and, more particularly, to a curved laser probe with single-use optic fiber.

BACKGROUND OF THE INVENTION

A wide variety of ophthalmic procedures require a laser energy source. For example, ophthalmic surgeons may use laser photocoagulation to treat proliferative retinopathy. Proliferative retinopathy is a condition characterized by the development of abnormal blood vessels in the retina that grow into the vitreous humor. Ophthalmic surgeons may treat this condition by energizing a laser to cauterize portions of the retina to prevent the abnormal blood vessels from growing and hemorrhaging. Typically, treatments are performed using a disposable, single-use laser probe connected to a laser surgical machine by an optical fiber. Unfortunately, use of disposable, single-use laser probes increases treatment costs because a new laser probe is required for each surgical treatment. Accordingly, there is a need for a laser probe that may be safely used to perform more than one surgical procedure.

BRIEF SUMMARY OF THE INVENTION

The present disclosure provides a curved laser probe with single-use optic fiber. In one or more embodiments, a curved laser probe with single-use optic fiber may comprise a reusable handle, an optic fiber fixture, and a single-use optic fiber. Illustratively, the single-use optic fiber may comprise an optic fiber having an optic fiber distal end and an optic fiber proximal end. In one or more embodiments, the optic fiber may be disposed in a first transitory connector having a first transitory connector distal end and a first transitory connector proximal end. Illustratively, the optic fiber may be disposed in the first transitory connector wherein the optic fiber distal end extends a fixed distance from the transitory connector distal end. In one or more embodiments, the optic fiber may be disposed in a second transitory connector having a second transitory connector distal end and a second transitory connector proximal end. Illustratively, the optic fiber may be disposed in the second transitory connector wherein the optic fiber proximal end extends a fixed distance from the second transitory connector distal end. In one or more embodiments, the first transitory connector may be inserted in the reusable handle and the second transitory connector may be inserted in the optic fiber fixture. Illustratively, the reusable handle may comprise a curved hypodermic tube.

BRIEF DESCRIPTION OF THE DRAWINGS

The above and further advantages of the present invention may be better understood by referring to the following description in conjunction with the accompanying drawings in which like reference numerals indicate identical or functionally similar elements:

FIGS. 7A, 7B, 7C, 7D, 7E, and 7F are schematic diagrams illustrating a curved hypodermic tube;

FIGS. 9A and 9B are schematic diagrams illustrating an assembled reusable handle;

DETAILED DESCRIPTION OF AN ILLUSTRATIVE EMBODIMENT

Figure 1A:
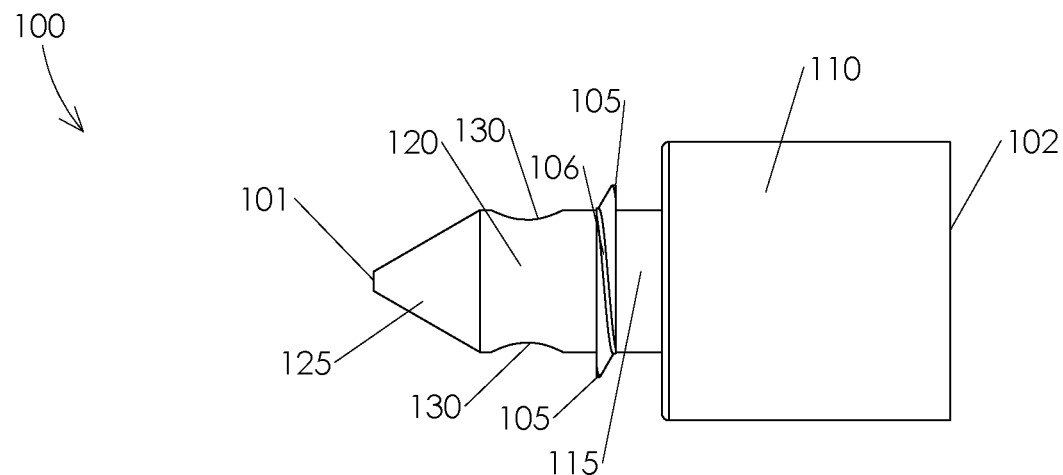
FIGS. 1A and 1B are schematic diagrams illustrating a transitory connector.
Figure 1B:
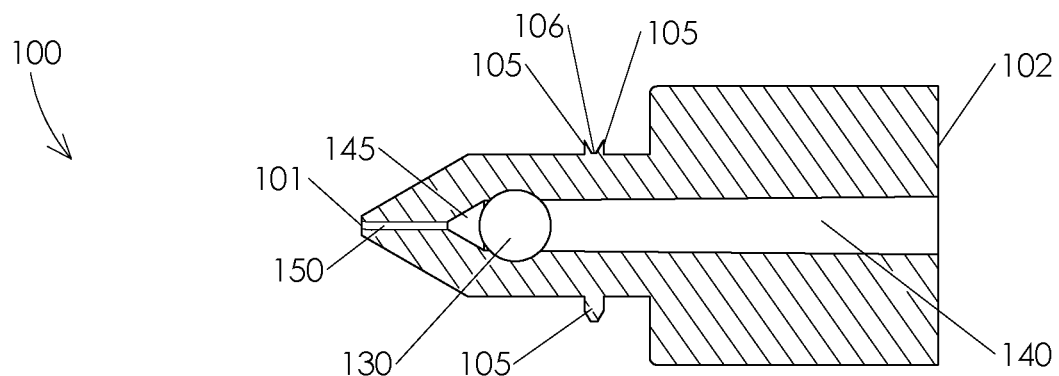

FIGS. 1A and 1B are schematic diagrams illustrating a transitory connector 100. FIG. 1A illustrates a side view of a transitory connector 100. FIG. 1B illustrates a cross-sectional view in a transverse plane of a transitory connector 100. In one or more embodiments, transitory connector 100 may comprise a transitory connector distal end 101 and a transitory connector proximal end 102. Illustratively, transitory connector 100 may comprise a major diameter 105 and a minor diameter 106. In one or more embodiments, transitory connector 100 may comprise a proximal base 110, a distal base 115, a nosecone base 120, and a nosecone 125. Illustratively, major diameter 105 may be disposed between distal base 115 and nosecone base 120. In one or more embodiments, minor diameter 106 may be disposed between distal base 115 and nosecone base 120. Illustratively, distal base 115 may be disposed between proximal base 110 and nosecone base 120. In one or more embodiments, nosecone base 120 may be disposed between distal base 115 and nosecone 125. Illustratively, transitory connector 100 may comprise an access lumen 130. In one or more embodiments, transitory connector 100 may comprise an inner bore 140. Illustratively, transitory connector 100 may comprise an inner bore distal taper 145. In one or more embodiments, transitory connector 100 may comprise an optic fiber housing 150. Illustratively, access lumen 130 may be disposed between inner bore 140 and inner bore distal taper 145. In one or more embodiments, inner bore distal taper 145 may be disposed between optic fiber housing 150 and access lumen 130. Illustratively, access lumen 130 may be disposed between optic fiber housing 150 and inner bore 140. In one or more embodiments, major diameter 105 may comprise a screw thread. Illustratively, minor diameter 106 may comprise a screw thread.

In one or more embodiments, transitory connector 100 may be manufactured from a material configured to deform if transitory connector 100 is sterilized in a medical autoclave, e.g., transitory connector 100 may be manufactured from a material configured to permanently deform if transitory connector 100 is sterilized in a medical autoclave. Illustratively, transitory connector 100 may be manufactured from a material having a melting point below a temperature parameter for a steam sterilization cycle, e.g., transitory connector 100 may be manufactured from a material having a melting point below a temperature parameter for a gravity-displacement steam sterilization cycle, a dynamic-air-removal steam sterilization cycle, etc. In one or more embodiments, transitory connector 100 may be manufactured from a material having a melting point below 140.0 degrees Fahrenheit. Illustratively, transitory connector 100 may be manufactured from a material having a melting point in a range of 158.0 to 212.0 degrees Fahrenheit, e.g., transitory connector 100 may be manufactured from a material having a melting point of 160.0 degrees Fahrenheit. In one or more embodiments, transitory connector 100 may be manufactured from a material having a melting point of less than 158.0 degrees Fahrenheit or greater than 212.0 degrees Fahrenheit. In one or more embodiments, transitory connector 100 may be manufactured from a material having a melting point below 250.0 degrees Fahrenheit. Illustratively, transitory connector 100 may be manufactured from a material having a melting point below 270.0 degrees Fahrenheit. In one or more embodiments, transitory connector 100 may be manufactured from a material having a melting point below 275.0 degrees Fahrenheit.

Illustratively, transitory connector 100 may be manufactured from a material configured to temporarily deform if transitory connector 100 is sterilized in a medical autoclave, e.g., transitory connector 100 may be manufactured from a material configured to absorb water in a medical autoclave. In one or more embodiments, an absorption of water may be configured to deform transitory connector 100, e.g., an absorption of water may be configured to cause transitory connector 100 to expand. Illustratively, transitory connector 100 may be manufactured from a porous material configured to facilitate a deformation of transitory connector 100 if transitory connector 100 is sterilized in a medical autoclave. In one or more embodiments, transitory connector 100 may be manufactured with one or more cavities configured to facilitate a deformation of transitory connector 100 if transitory connector 100 is sterilized in a medical autoclave. Illustratively, transitory connector 100 may be manufactured from any suitable material, e.g., polymers, metals, metal alloys, etc., or from any combination of suitable materials. In one or more embodiments, transitory connector 100 may be manufactured by a 3D printing process. For example, transitory connector 100 may be manufactured by selective laser sintering, selective heat sintering, selective laser melting, electron-beam melting, direct metal laser sintering, electron beam freeform fabrication, etc. Illustratively, transitory connector 100 may be manufactured by injection molding. In one or more embodiments, transitory connector 100 may be manufactured by additive manufacturing.

In one or more embodiments, transitory connector 100 may be manufactured from poly(acrylamide), poly(acrylic acid), poly(adipic anhydride), poly(7-aminoenanthic acid), poly(12-aminolauric acid), poly(11-aminoundecanoic acid), poly(azelaic anhydride), poly[1,3-butadiene(1,4-)-alt-methacrylonitrile], poly[1,3-butadiene(1,4-)-alt-methyl methacrylate], poly(butadiene oxide), poly(caprylaldehyde), poly(1,4-cyclohexylenedimethylene azelate), poly(1,4-cyclohexylenedimethylene dodecanedioate), poly(1,4-cyclohexylenedimethylene glutarate), poly(1,4-cyclohexylenedimethylene p-phenylenediacetate), poly(1,4-cyclohexylenedimethylene pimelate), poly(1,4-cyclohexylenedimethylene sebacate), poly(1,4-cyclohexylenedimethylene suberate), poly(cyclohexylidenethiohexamethylene sulfide), poly(cyclopropylenedimethylene piperazinediurethane), poly(cyclopropylidenedimethylene oxide), poly(decamethylene), poly(decamethylene carbonate), poly[(decamethylenedioxy)-dihexamethylene oxide], poly(decamethylene disulfide), poly(decamethylenedithioethylene disulfide), poly(decamethylenedithiohexamethylene disulfide), poly(decamethylene dithioladipate), poly(decamethylenedithiotetramethylene disulfide), poly(decamethylene pimelate), poly(decamethylene fumaramide), poly(decamethylene glutaramide), poly(decamethylene isophthalate), poly(decamethylene malonate), poly(decamethylene oxydiacetate), poly(decamethyleneoxymethylene oxide), poly(decamethylene succinate), poly(decamethylene sulfide), poly(decamethylene thiodivalerate), poly(decamethylenethiohexamethylene sulfide), poly(divinylbenzal), poly(dodecamethylene), poly(dodecanedioic anhydride), poly(eicosamethylene adipate), poly(eicosamethylene azelate), poly(eicosamethylene glutarate), poly(eicosamethylene isophthalate), poly(eicosamethylene malonate), poly(eicosamethylene oxalate), poly(eicosamethylene oxydiacetate), poly(eicosamethylene phthalate), poly(eicosamethylene pimelate), poly(eicosamethylene sebacate), poly(eicosamethylene suberate), poly(eicosamethylene succinate), poly(eicosamethylene thiodivalerate), poly[ethylene p-(carboxyphenoxy)-butyrate], poly[ethylene p-(carboxyphenoxy)-caproate], poly[ethylene p-(carboxyphenoxy)-heptanoate], poly[ethylene p-(carboxyphenoxy)-undecanoate], poly[ethylene p-(carboxyphenoxy)-valerate], poly(ethylene 2,2'-dibenzoate), poly[(ethylenedioxy)-diethylene 2,2'-dibenzoate], poly(ethylene 2,2'-dibenzoate), poly[(ethylenedioxy)-diethylene 3,3'-dibenzoate], poly[(ethylenedioxy)-diethylene isophthalate], poly[(ethylenedioxy)-diethylene sebacate], poly[(ethylenedioxy)-diethylene thiodivalerate], poly(ethylene disiloxanylenedipropionamide), poly[(ethylenedithio)-diacetic anhydride], poly[(ethylenedithio)-dipropionic anhydride], poly(ethylene dithionisophthalate), poly(ethelene dithiotetramethylene disulfide), poly(ethylene fumaramide), poly(ethylene glutarate), poly(ethylene 2,4-hexadienediamide), poly(ethylene phthalate), poly(ethylene sulfonyldivalerate), poly(ethylene terephthalate), poly(heptamethylene), poly(hexamethylene azelate), poly(hexamethylene carbonate), poly[hexamethylene p-(carboxyphenoxy)-acetate], poly[hexamethylene p-(carboxyphenoxy)-caproate], poly[hexamethylene p-(carboxyphenoxy)-undecanoate], poly[hexamethylene p-(carboxyphenoxy)-valerate], poly(hexamethylene isophthalate), poly[hexamethylene (methylene-2,5-tetrahydrofuran)-dicarboxamide], poly(hexamethylene octadecanediamide), poly(hexamethylene oxydiacetate), poly(hexamethylene 4,4'-oxydibenzoate), poly(hexamethylene pimelate), poly(hexamethylene succinate), poly(hexamethylene thiodivalerate), poly(hexamethylenethiooentamethylene sulfide), poly(hexamethylenethiotetramethylene sulfide), poly(hexenamer), etc. Illustratively, transitory connector 100 may be manufactured from any substituted polymers of poly(acrylamide), poly(acrylic acid), poly(adipic anhydride), poly(7-aminoenanthic acid), poly(12-aminolauric acid), poly(11-aminoundecanoic acid), poly(azelaic anhydride), poly[1,3-butadiene(1,4-)-alt-methacrylonitrile], poly[1,3-butadiene(1,4-)-alt-methyl methacrylate], poly(butadiene oxide), poly(capryl aldehyde), poly(1,4-cyclohexylenedimethylene azelate), poly(1,4-cyclohexylenedimethylene dodecanedioate), poly(1,4-cyclohexylenedimethylene glutarate), poly(1,4-cyclohexylenedimethylene p-phenylenediacetate), poly(1,4-cyclohexylenedimethylene pimelate), poly(1,4- cyclohexylenedimethylene sebacate), poly(1,4-cyclohexylenedimethylene suberate), poly(cyclohexylidenethiohexamethylene sulfide), poly(cyclopropylenedimethylene piperazinediurethane), poly(cyclopropylidenedimethylene oxide), poly(decamethylene), poly(decamethylene carbonate), poly[(decamethylenedioxy)-dihexamethylene oxide], poly(decamethylene disulfide), poly(decamethylenedithioethylene disulfide), poly(decamethylenedithiohexamethylene disulfide), poly(decamethylene dithioladipate), poly(decamethylenedithiotetramethylene disulfide), poly(decamethylene pimelate), poly(decamethylene fumaramide), poly(decamethylene glutaramide), poly(decamethylene isophthalate), poly(decamethylene malonate), poly(decamethylene oxydiacetate), poly(decamethyleneoxymethylene oxide), poly(decamethylene succinate), poly(decamethylene sulfide), poly(decamethylene thiodivalerate), poly(decamethylenethiohexamethylene sulfide), poly(divinylbenzal), poly(dodecamethylene), poly(dodecanedioic anhydride), poly(eicosamethylene adipate), poly(eicosamethylene azelate), poly(eicosamethylene glutarate), poly(eicosamethylene isophthalate), poly(eicosamethylene malonate), poly(eicosamethylene oxalate), poly(eicosamethylene oxydiacetate), poly(eicosamethylene phthalate), poly(eicosamethylene pimelate), poly(eicosamethylene sebacate), poly(eicosamethylene suberate), poly(eicosamethylene succinate), poly(eicosamethylene thiodivalerate), poly[ethylene p-(carboxyphenoxy)-butyrate], poly[ethylene p-(carboxyphenoxy)-caproate], poly[ethylene p-(carboxyphenoxy)-heptanoate], poly[ethylene p-(carboxyphenoxy)-undecanoate], poly[ethylene p-(carboxyphenoxy)-valerate], poly(ethylene 2,2'-dibenzoate), poly[(ethylenedioxy)-diethylene 2,2'-dibenzoate], poly(ethylene 2,2'-dibenzoate), poly[(ethylenedioxy)-diethylene 3,3'-dibenzoate], poly[(ethylenedioxy)-diethylene isophthalate], poly[(ethylenedioxy)-diethylene sebacate], poly[(ethylenedioxy)-diethylene thiodivalerate], poly(ethylene disiloxanylenedi-propionamide), poly[(ethylenedithio)-diacetic anhydride], poly[(ethylenedithio)-dipropionic anhydride], poly(ethylene dithionisophthalate), poly(ethelene dithiotetra-methylene disulfide), poly(ethylene fumaramide), poly(ethylene glutarate), poly(ethylene 2,4-hexadienediamide), poly(ethylene phthalate), poly(ethylene sulfonyldivalerate), poly(ethylene terephthalate), poly(heptamethylene), poly(hexamethylene azelate), poly(hexamethylene carbonate), poly[hexamethylene p-(carboxyphenoxy)-acetate], poly[hexamethylene p-(carboxyphenoxy)-caproate], poly[hexamethylene p-(carboxyphenoxy)-undecanoate], poly[hexamethylene p-(carboxyphenoxy)-valerate], poly(hexamethylene isophthalate), poly[hexamethylene (methylene-2,5-tetrahydrofuran)-dicarboxamide], poly(hexamethylene octadecanediamide), poly(hexamethylene oxydi-acetate), poly(hexamethylene 4,4'-oxydibenzoate), poly(hexamethylene pimelate), poly(hexamethylene succinate), poly(hexamethylene thiodivalerate), poly(hexamethylenethiooentamethylene sulfide), poly(hexamethylenethiotetramethylene sulfide), poly(hexenamer), etc.

Figure 2:
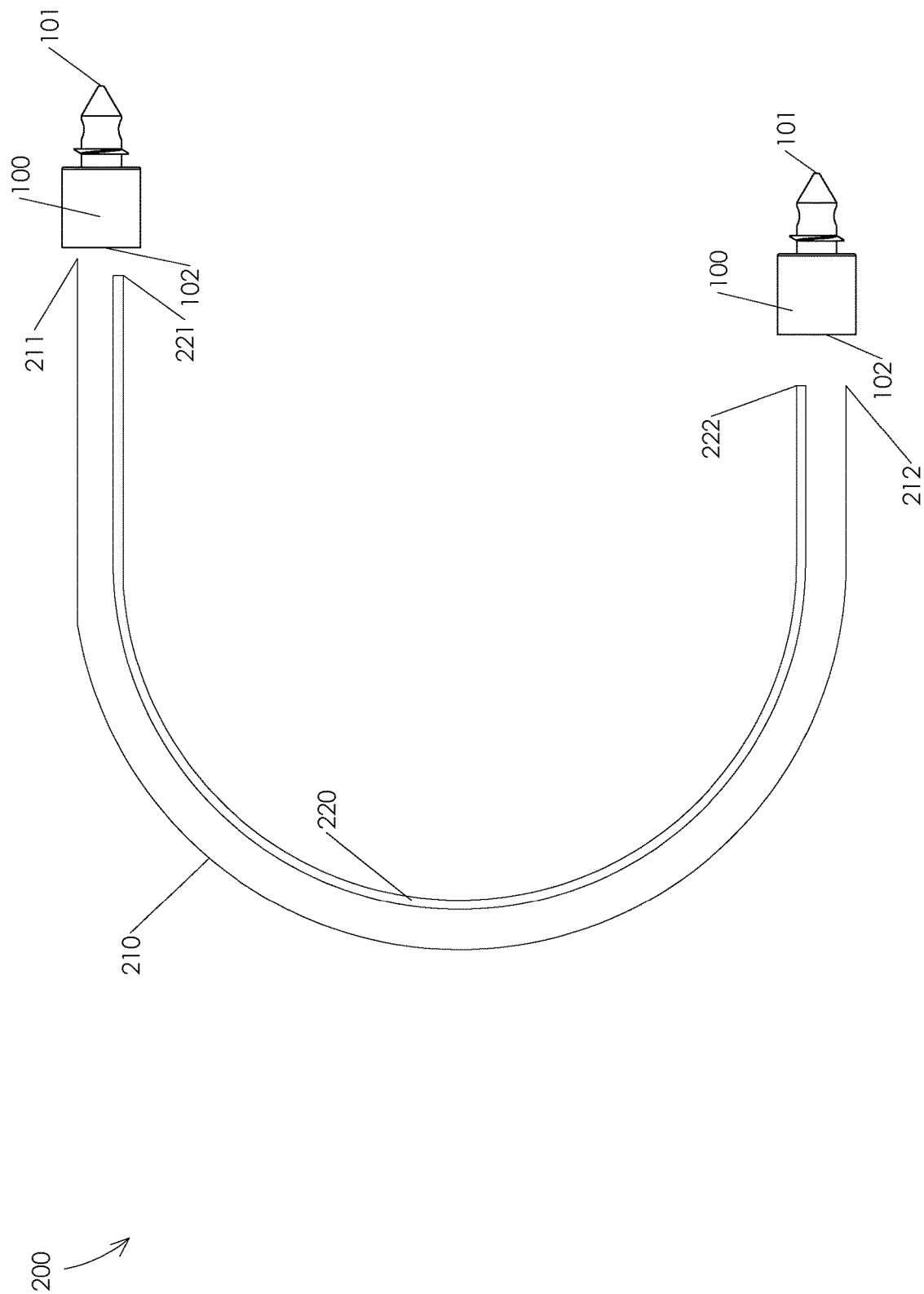
FIG. 2 is a schematic diagram illustrating an exploded view of a single-use optic fiber assembly.

FIG. 2 is a schematic diagram illustrating an exploded view of a single-use optic fiber assembly 200. Illustratively, a single-use optic fiber assembly 200 may comprise a first transitory connector 100, an optic fiber 210, jacketing 220, and a second transitory connector 100. In one or more embodiments, optic fiber 210 may comprise an optic fiber distal end 211 and an optic fiber proximal end 212. Illustratively, optic fiber 210 may be configured to transmit laser light. In one or more embodiments, jacketing 220 may comprise a jacketing distal end 221 and a jacketing proximal end 222. Illustratively, jacketing 220 may be manufactured from any suitable material, e.g., polymers, metals, metal alloys, etc., or from any combination of suitable materials.

Figure 3A:
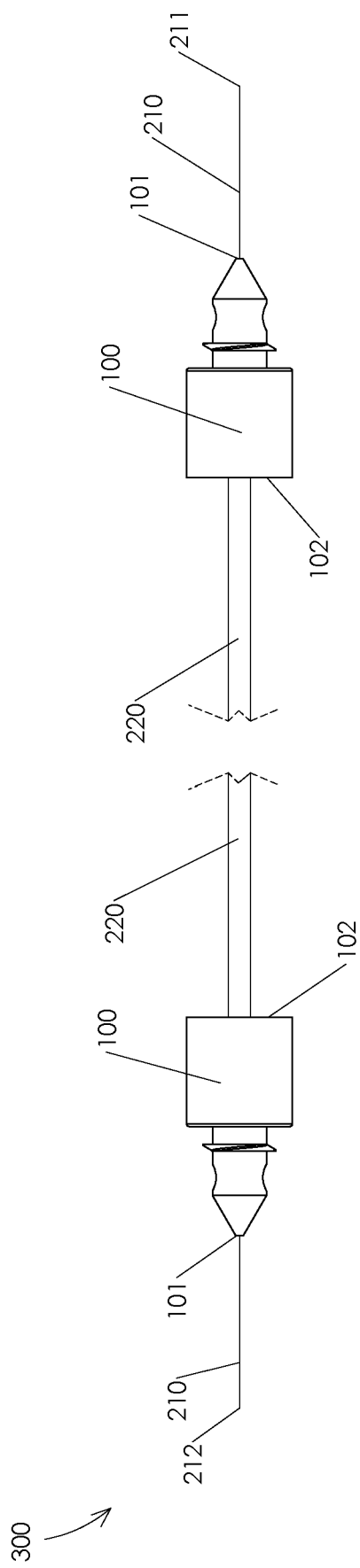
FIGS. 3A and 3B are schematic diagrams illustrating an assembled single-use optic fiber.
Figure 3B:
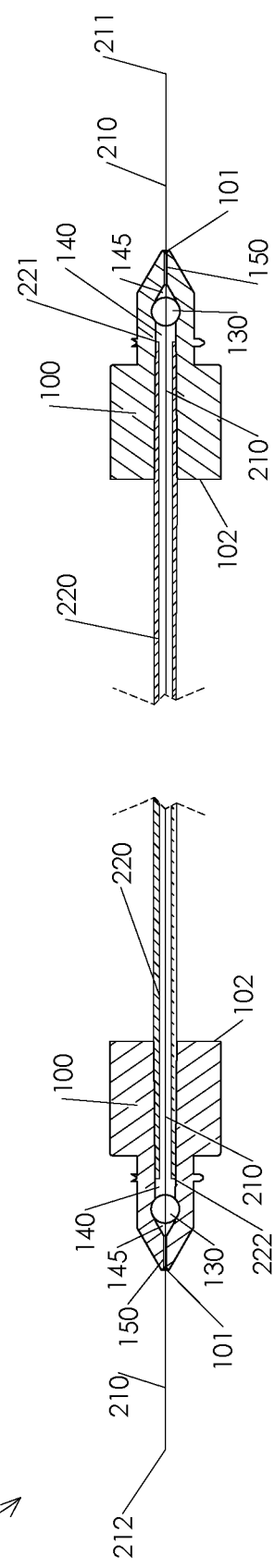

FIGS. 3A and 3B are schematic diagrams illustrating an assembled single-use optic fiber 300. FIG. 3A illustrates a side view of an assembled single-use optic fiber 300. FIG. 3B illustrates a cross-sectional view in a transverse plane of an assembled single-use optic fiber 300. Illustratively, optic fiber proximal end 212 may extend a distance from first transitory connector distal end 101. In one or more embodiments, optic fiber distal end 211 may extend a distance from second transitory connector distal end 101. Illustratively, optic fiber 210 may be disposed within jacketing 220 wherein optic fiber distal end 211 extends a distance from jacketing distal end 221 and wherein optic fiber proximal end 212 extends a distance from jacketing proximal end 222. In one or more embodiments, a portion of jacketing 220 may be disposed in a portion of first transitory connector 100, e.g., jacketing proximal end 222 may be disposed in inner bore 140. Illustratively, a portion of jacketing 220 may be fixed in a portion of first transitory connector 100, e.g., a portion of jacketing 220 may be fixed in a portion of first transitory connector 100 by an adhesive, a friction fit, a crimp, a tie, a weld, etc. In one or more embodiments, a portion of jacketing 220 may be disposed in a portion of second transitory connector 100, e.g., jacketing distal end 221 may be disposed in inner bore 140. Illustratively, a portion of jacketing 220 may be fixed in a portion of second transitory connector 100, e.g., a portion of jacketing 220 may be fixed in a portion of second transitory connector 100 by an adhesive, an epoxy, a friction fit, a crimp, a tie, a weld, etc.

In one or more embodiments, a portion of optic fiber 210 may be disposed in first transitory connector 100 wherein optic fiber 210 is disposed in inner bore 140, access lumen 130, inner bore distal taper 145, and optic fiber housing 150. Illustratively, a portion of optic fiber 210 may be fixed in a portion of first transitory connector 100, e.g. a portion of optic fiber 210 may be fixed in optic fiber housing 150. In one or more embodiments, a portion of optic fiber 210 may be fixed in optic fiber housing 150, e.g., a portion of optic fiber 210 may be fixed in optic fiber housing 150 by an adhesive, an epoxy, a friction fit, a tie, a crimp, a weld, etc. Illustratively, a portion of optic fiber 210 may be fixed in first transitory connector 100 wherein optic fiber proximal end 212 extends a distance from first transitory connector distal end 101. In one or more embodiments, a portion of optic fiber 210 may be disposed in second transitory connector 100 wherein optic fiber 210 is disposed in inner bore 140, access lumen 130, inner bore distal taper 145, and optic fiber housing 150. Illustratively, a portion of optic fiber 210 may be fixed in a portion of second transitory connector 100, e.g. a portion of optic fiber 210 may be fixed in optic fiber housing 150. In one or more embodiments, a portion of optic fiber 210 may be fixed in optic fiber housing 150, e.g., a portion of optic fiber 210 may be fixed in optic fiber housing 150 by an adhesive, an epoxy, a friction fit, a tie, a crimp, a weld, etc. Illustratively, a portion of optic fiber 210 may be fixed in second transitory connector 100 wherein optic fiber distal end 211 extends a distance from second transitory connector distal end 101. Illustratively, a distance that optic fiber distal end 211 extends from second transitory connector distal end 101 may be identical to a distance that optic fiber proximal end 212 extends from first transitory connector distal end 101. In one or more embodiments, a distance that optic fiber distal end 211 extends from second transitory connector distal end 101 and a distance that optic fiber proximal end 212 extends from first transitory connector distal end 101 may be configured to allow first transitory connector 100 and second transitory connector 100 to be interchangeable.

Figure 4:
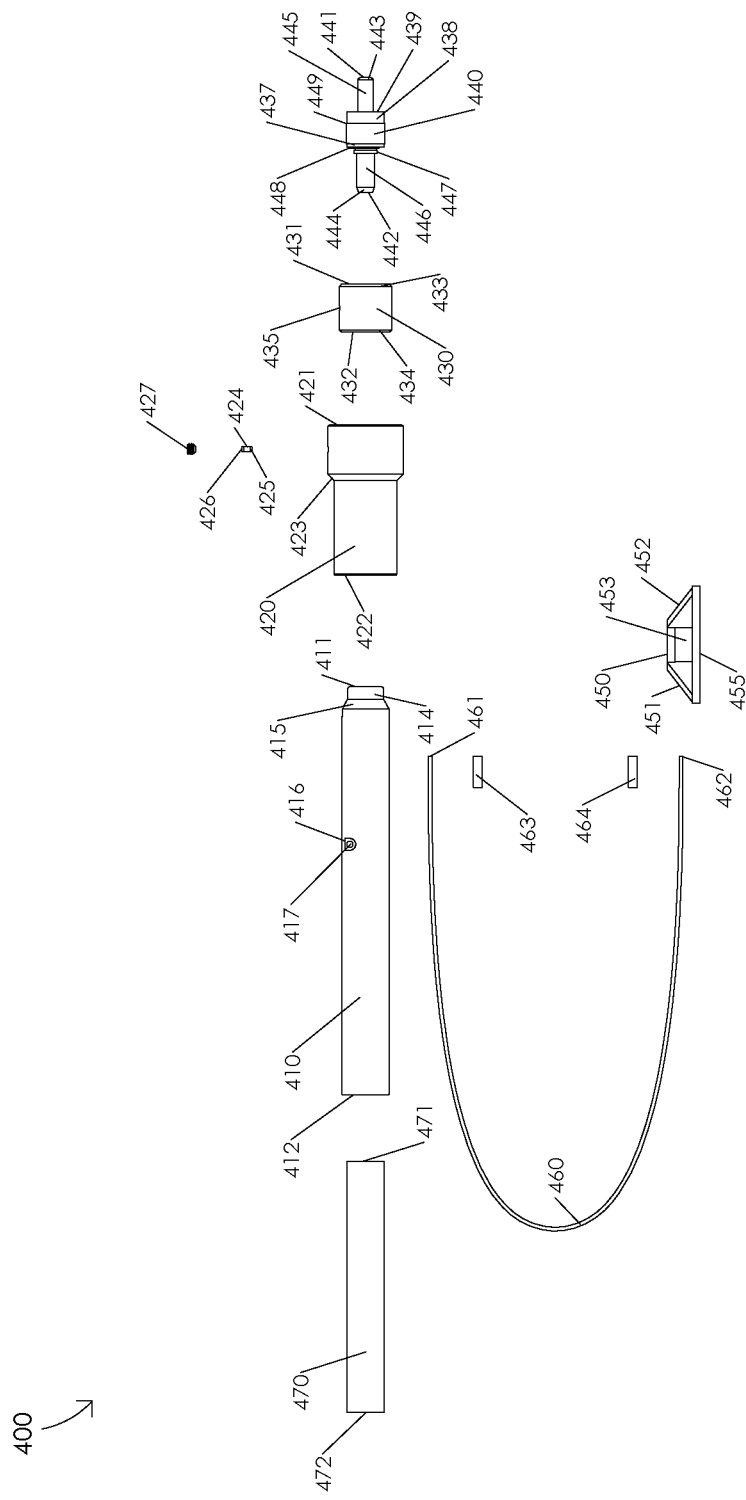
FIG. 4 is a schematic diagram illustrating an exploded view of an optic fiber fixture assembly.

FIG. 4 is a schematic diagram illustrating an exploded view of an optic fiber fixture assembly 400. Illustratively, an optic fiber fixture assembly 400 may comprise a fixture base 410, a machine connector housing 420, an electrical element 424, a fixation mechanism 427, an extender 430, a machine connector 440, a machine coupler 450, a lanyard cable 460, a distal fastener 463, a proximal fastener 464, and a fixture facilitating sleeve 470. In one or more embodiments, fixture base 410 may comprise a fixture base distal end 411 and a fixture base proximal end 412. Illustratively, fixture base 410 may comprise an extender interface 414, a fixture base distal taper 415, an indentation 416, and a lanyard cable guide 417. In one or more embodiments, lanyard cable guide 417 may be disposed in indentation 416. Illustratively, lanyard cable guide 417 may be disposed dorsally in fixture base 410. In one or more embodiments, machine connector housing 420 may comprise a machine connector housing distal end 421 and a machine connector housing proximal end 422. Illustratively, machine connector housing 420 may comprise a machine connector housing taper 423. In one or more embodiments, extender 430 may comprise an extender distal end 431 and an extender proximal end 432. Illustratively, extender 430 may comprise an extender distal taper 433 and an extender proximal taper 434. In one or more embodiments, extender 430 may comprise an electrical element housing 435. Illustratively, electrical element housing 435 may be configured to house electrical element 424. In one or more embodiments, electrical element 424 may comprise an electrical element inferior end 425 and an electrical element superior end 426.

In one or more embodiments, machine connector 440 may comprise a machine connector distal end 441 and a machine connector proximal end 442. Illustratively, machine connector 440 may comprise a machine connector distal taper 443, a machine connector proximal taper 444, a distal ferrule 445, and a proximal ferrule 446. In one or more embodiments, machine connector 440 may comprise a machine connector base 438. Illustratively, machine connector base 438 may comprise a machine connector base distal end 439 and a machine connector base proximal end 449. In one or more embodiments, machine connector 440 may comprise a retaining ring distal interface 437, a retaining ring proximal interface 447, and a retaining ring 448. Illustratively, retaining ring 448 may be disposed between retaining ring distal interface 437 and retaining ring proximal interface 447. In one or more embodiments, lanyard cable 460 may comprise a lanyard cable distal end 461 and a lanyard cable proximal end 462. Illustratively, machine coupler 450 may comprise a machine coupler inferior end 451 and a machine coupler superior end 452. In one or more embodiments, machine coupler 450 may comprise a machine coupler aperture 453. Illustratively, machine coupler 450 may comprise a machine interface 455.

In one or more embodiments, fixture facilitating sleeve 470 may comprise a fixture facilitating sleeve distal end 471 and a fixture facilitating sleeve proximal end 472. Illustratively, fixture facilitating sleeve 470 may be manufactured from a material configured to minimize a coefficient of friction between a portion of optic fiber 210 and a portion of fixture facilitating sleeve 470, e.g., fixture facilitating sleeve 470 may be manufactured from a self-lubricating thermoplastic material. In one or more embodiments, fixture facilitating sleeve 470 may be manufactured from a material wherein a coefficient of friction between a portion of optic fiber 210 and a portion of fixture facilitating sleeve 470 is in a range of 0.011 to 0.36, e.g., fixture facilitating sleeve 470 may be manufactured from a material wherein a coefficient of friction between a portion of optic fiber 210 and a portion of fixture facilitating sleeve 470 is 0.0311. Illustratively, fixture facilitating sleeve 470 may be manufactured from a material wherein a coefficient of friction between a portion of optic fiber 210 and a portion of fixture facilitating sleeve 470 is less than 0.011 or greater than 0.36. In one or more embodiments, fixture facilitating sleeve 470 may be manufactured from a fluorocarbon material, e.g., fixture facilitating sleeve 470 may be manufactured from a polytetrafluoroethylene material. Illustratively, fixture facilitating sleeve 470 may be manufactured from an acetal-based polytetrafluoroethylene material, e.g., fixture facilitating sleeve 470 may be manufactured from a turcite material. In one or more embodiments, fixture facilitating sleeve 470 may be manufactured from a material having a density in a range of 0.024 to 0.073 pounds per cubic inch, e.g., fixture facilitating sleeve 470 may be manufactured from a material having a density of 0.053 pounds per cubic inch. Illustratively, fixture facilitating sleeve 470 may be manufactured from a material having a density of less than 0.024 pounds per cubic inch or greater than 0.073 pounds per cubic inch. In one or more embodiments, fixture facilitating sleeve 470 may be manufactured from a material having a hardness in a range of 50 Shore D to 75 Shore D, e.g., fixture facilitating sleeve 470 may be manufactured from a material having a hardness of 61 Shore D. Illustratively, fixture facilitating sleeve 470 may be manufactured from a material having a hardness of less than 50 Shore D or greater than 75 Shore D. In one or more embodiments, optic fiber 210 may be manufactured from a material having a first hardness and fixture facilitating sleeve 470 may be manufactured from a material having a second hardness. Illustratively, the first hardness may be greater than the second hardness. In one or more embodiments, optic fiber 210 may be manufactured from a material having a first hardness, fixture facilitating sleeve 470 may be manufactured from a material having a second hardness, and transitory connector 100 may be manufactured from a material having a third hardness. Illustratively, the first hardness may be greater than the second hardness and the second hardness may be greater than the third hardness.

Figure 5A:
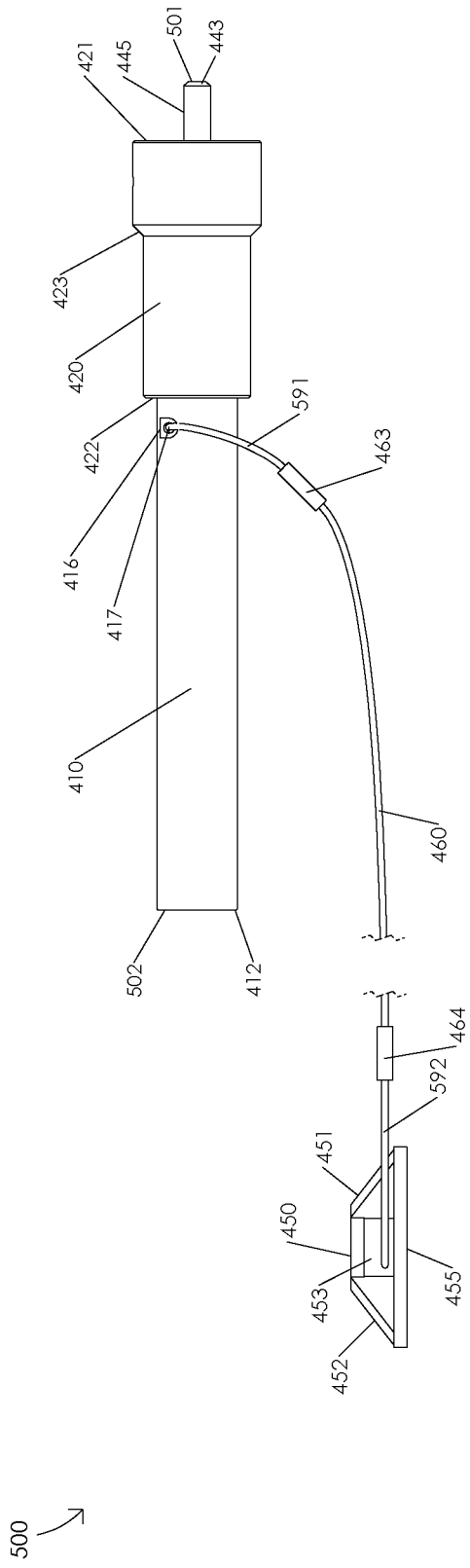
FIGS. 5A and 5B are schematic diagrams illustrating an assembled optic fiber fixture.
Figure 5B:
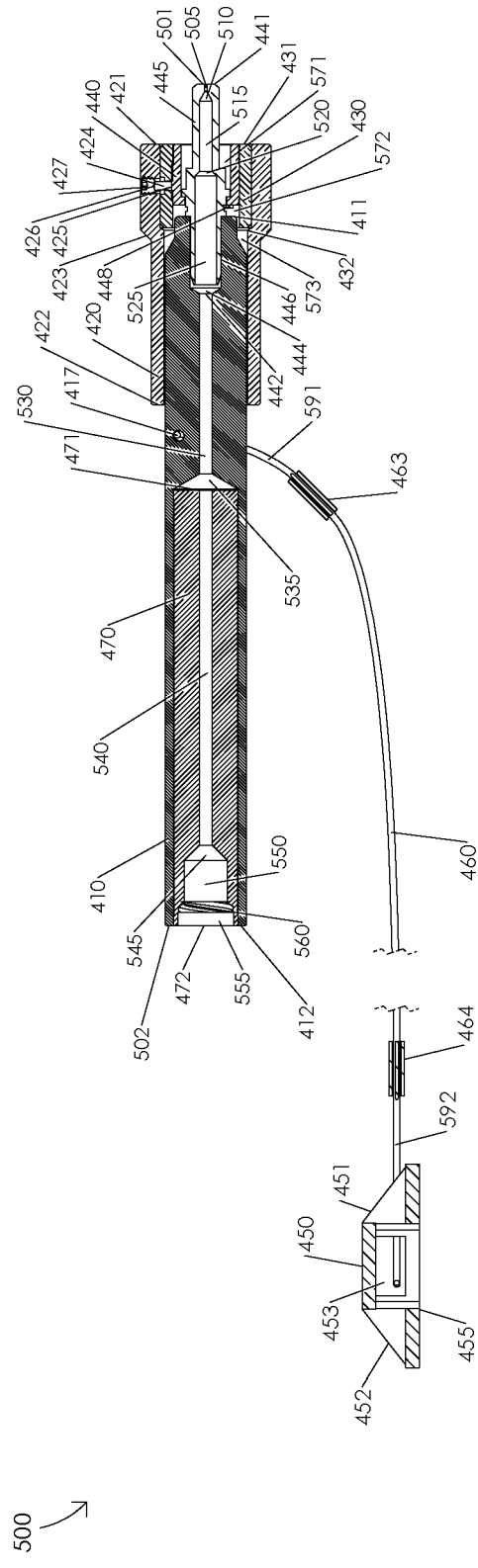

FIGS. 5A and 5B are schematic diagrams illustrating an assembled optic fiber fixture 500. FIG. 5A illustrates a side view of an assembled optic fiber fixture 500. FIG. 5B illustrates a cross-sectional view in a sagittal plane of an assembled optic fiber fixture 500. Illustratively, an assembled optic fiber fixture 500 may comprise an assembled optic fiber fixture distal end 501 and an assembled optic fiber fixture proximal end 502. In one or more embodiments, assembled optic fiber fixture 500 may comprise an optic fiber proximal end guide 505, an inner lumen distal taper 510, a machine connector distal inner lumen 515, an inner lumen proximal taper 520, a machine connector proximal inner lumen 525, a fixture base inner bore 530, a fixture facilitating sleeve housing 535, a fixture facilitating sleeve inner bore 540, a first transitory connector housing distal taper 545, a first transitory connector housing 550, a first transitory connector housing proximal chamber 555, and a first transitory connector housing threading 560.

Illustratively, fixture facilitating sleeve 470 may be disposed in a portion of fixture base 410, e.g., fixture facilitating sleeve 470 may be disposed in fixture facilitating sleeve housing 535. In one or more embodiments, fixture facilitating sleeve 470 may be disposed in a portion of fixture base 410 wherein fixture facilitating sleeve proximal end 472 is adjacent to fixture base proximal end 412, e.g., fixture facilitating sleeve 470 may be disposed in a portion of fixture base 410 wherein fixture facilitating sleeve proximal end 472 abuts fixture base proximal end 412. Illustratively, fixture facilitating sleeve 470 may be disposed in a portion of fixture base 410 wherein fixture facilitating sleeve inner bore 540 is aligned with fixture base inner bore 530, e.g., fixture facilitating sleeve 470 may be disposed in a portion of fixture base 410 wherein fixture facilitating sleeve inner bore 540 is collinear with fixture base inner bore 530. In one or more embodiments, fixture facilitating sleeve 470 may be disposed in a portion of fixture base 410 wherein fixture facilitating sleeve 470 is fixed in the portion of fixture base 410, e.g., fixture facilitating sleeve 470 may be fixed in a portion of fixture base 410 by an adhesive, an epoxy, a friction fit, a crimp, a tie, a weld, etc. In one or more embodiments, fixture facilitating sleeve 470 may be fixed in fixture facilitating sleeve housing 535, e.g., fixture facilitating sleeve 470 may be fixed in fixture facilitating sleeve housing 535 by an adhesive, an epoxy, a friction fit, a crimp, a tie, a weld, etc.

In one or more embodiments, lanyard cable 460 may comprise a distal loop 591 and a proximal loop 592. Illustratively, distal fastener 463 may be disposed over a portion of lanyard cable 460 wherein lanyard cable distal end 461 extends a distance from distal fastener 463. In one or more embodiments, lanyard cable distal end 461 may be threaded through lanyard cable guide 417 and into a portion of distal fastener 463 to form distal loop 591. Illustratively, distal fastener 463 may be configured to fix lanyard cable distal end 461 within distal fastener 463, e.g., distal fastener 463 may be configured to fix lanyard cable distal end 461 within distal fastener 463 by an adhesive, a crimp, a weld, a friction fit, etc. In one or more embodiments, proximal fastener 464 may be disposed over a portion of lanyard cable 460 wherein lanyard cable proximal end 462 extends a distance from proximal fastener 464. Illustratively, lanyard cable proximal end 462 may be threaded through machine coupler aperture 453 and into a portion of proximal fastener 464 to form proximal loop 592. In one or more embodiments, proximal fastener 464 may be configured to fix lanyard cable proximal end 462 within proximal fastener 464, e.g., proximal fastener 464 may be configured to fix lanyard cable proximal end 462 within proximal fastener 464 by an adhesive, an epoxy, a crimp, a weld, a friction fit, etc.

Illustratively, machine connector 440 may comprise a machine connector inner chamber 571. In one or more embodiments, distal ferrule 445 may extend a distance out from machine connector inner chamber 571. Illustratively, extender 430 may comprise an extender inner chamber 572. In one or more embodiments, machine connector 440 may be disposed in extender inner chamber 572. Illustratively, machine connector 440 may be disposed in extender 430, e.g., machine connector 440 may be disposed in extender 430 wherein machine connector distal end 441 may extend a distance from extender distal end 431 and wherein machine connector proximal end 442 may extend a distance from extender proximal end 432. In one or more embodiments, machine connector 440 may be fixed in extender 430, e.g., machine connector 440 may be fixed in extender 430 by an adhesive, a crimp, a weld, a friction fit, etc. Illustratively, machine connector housing 420 may comprise a machine connector housing inner chamber 573. In one or more embodiments, extender 430 may be disposed in machine connector housing inner chamber 573. Illustratively, extender 430 may be disposed in machine connector housing 420, e.g., extender 430 may be disposed in machine connector housing 420 wherein extender distal end 431 is disposed between machine connector housing distal end 421 and machine connector housing proximal end 422 and wherein extender proximal end 432 is disposed between machine connector housing distal end 421 and machine connector housing proximal end 422. In one or more embodiments, extender 430 may be disposed in machine connector housing 420 wherein machine connector distal end 441 extends a distance from machine connector housing distal end 421, e.g., extender may be disposed in machine connector housing 420 wherein machine connector proximal end 442 may be disposed between machine connector housing distal end 421 and machine connector housing proximal end 422. Illustratively, extender 430 may be fixed in machine connector housing 420, e.g., extender 430 may be fixed in machine connector housing 420 by an adhesive, an epoxy, a crimp, a weld, a friction fit, etc.

In one or more embodiments, fixture base 410 may be disposed in machine connector housing 420, e.g., fixture base 410 may be disposed in machine connector housing 420 wherein fixture base proximal end 412 extends a distance from machine connector housing proximal end 422 and wherein fixture base distal end 411 is disposed between machine connector housing distal end 421 and machine connector housing proximal end 422. Illustratively, fixture base 410 may be fixed in machine connector housing 420, e.g., fixture base 410 may be fixed in machine connector housing 420 by an adhesive, a crimp, a weld, a friction fit, etc. In one or more embodiments, fixture base 410 may be disposed in extender 430, e.g., fixture base 410 may be disposed in extender 430 wherein fixture base proximal end 412 extends a distance from extender proximal end 432 and wherein fixture base distal end 411 is disposed between extender distal end 431 and extender proximal end 432. Illustratively, fixture base 410 may be fixed in extender 430, e.g., fixture base 410 may be fixed in extender 430 by an adhesive, a crimp, a weld, a friction fit, etc. In one or more embodiments, machine connector 440 may be disposed in fixture base 410, e.g., machine connector 440 may be disposed in fixture base 410 wherein machine connector distal end 441 extends a distance from fixture base distal end 411 and wherein machine connector proximal end 442 is disposed between fixture base distal end 411 and fixture base proximal end 412. Illustratively, machine connector 440 may be fixed in fixture base 410, e.g., machine connector 440 may be fixed in fixture base 410 by an adhesive, an epoxy, a crimp, a weld, a friction fit, etc.

In one or more embodiments, electrical element 424 may be disposed in machine connector housing 420 and extender 430, e.g., electrical element may be disposed in electrical element housing 435. Illustratively, electrical element 424 may be fixed in electrical element housing 435, e.g., electrical element 424 may be fixed in electrical element housing 435 by an adhesive, an epoxy, a crimp, a weld, a friction fit, etc. In one or more embodiments, electrical element 424 may be disposed in machine connector housing 420 and extender 430 wherein electrical element inferior end 425 may be in contact with machine connector 440, e.g., electrical element 424 may be disposed in electrical element housing 435 wherein electrical element inferior end 425 may be in contact with machine connector 440. Illustratively, electrical element 424 may be electrically connected to machine connector 440. In one or more embodiments, electrical element 424 may be configured to convey data to a machine, e.g., electrical element 424 may be configured to convey data to a laser machine. Illustratively, electrical element 424 may comprise a resistor, e.g., electrical element 424 may comprise a cylindrical resistor. In one or more embodiments, electrical element 424 may comprise a radio frequency identification chip.

Illustratively, fixation mechanism 427 may be disposed in machine connector housing 420, e.g., fixation mechanism 427 may be disposed in machine connector housing 420 wherein a portion of fixation mechanism 427 contacts a portion of electrical element 424. In one or more embodiments, fixation mechanism 427 may be fixed in machine connector housing 420, e.g., fixation mechanism 427 may be fixed in machine connector housing 420 by an adhesive, an epoxy, a crimp, a weld, a friction fit, etc. Illustratively, fixation mechanism 427 may be configured to fix electrical element 424 in electrical element housing 435, e.g., fixation mechanism 427 may comprise a setscrew configured to fix electrical element 424 in electrical element housing 435. In one or more embodiments, fixation mechanism 427 may be electrically conductive. Illustratively, fixation mechanism 427 may be disposed in machine connector housing 420 wherein fixation mechanism 427 contacts electrical element 424 and electrical element 424 contacts machine connector 440, e.g., fixation mechanism 427 may be disposed in machine connector housing 420 wherein fixation mechanism 427 contacts electrical element superior end 426 and electrical element inferior end 425 contacts machine connector 440. In one or more embodiments, fixation mechanism 427 may be disposed in machine connector housing 420 wherein fixation mechanism 427 is electrically connected to electrical element 424 and electrical element 424 is electrically connected to machine connector 440.

Illustratively, machine coupler 450 may be configured to attach assembled optic fiber fixture 500 to a laser machine, e.g., machine interface 455 may be configured to attach assembled optic fiber fixture 500 to a laser machine. In one or more embodiments, machine interface 455 may comprise a magnet configured to attach assembled optic fiber fixture 500 to a laser machine. Illustratively, machine interface 455 may comprise an adhesive configured to attach assembled optic fiber fixture 500 to a laser machine. In one or more embodiments, assembled optic fiber fixture 500 may be reusable, e.g., assembled optic fiber fixture 500 may be sold non-sterile and not intended to be sterilized by a user in a medical autoclave. Illustratively, a user may clean assembled optic fiber fixture 500 by flushing assembled optic fiber fixture 500 with a syringe of isopropyl alcohol. In one or more embodiments, flushing assembled optic fiber fixture 500 with a syringe of isopropyl alcohol before each use of assembled optic fiber fixture 500 may be configured to remove any particulate matter that may have accumulated in assembled optic fiber fixture 500 since a previous use of assembled optic fiber fixture 500. Illustratively, optic fiber fixture 500 may comprise an end cap configured to fit over optic fiber fixture proximal end 502, e.g., optic fiber fixture 500 may comprise an end cap configured to fit over optic fiber fixture proximal end 502 to prevent particulate matter from accumulating in optic fiber fixture 500 when optic fiber fixture 500 is not being used by a user.

Figure 6A:
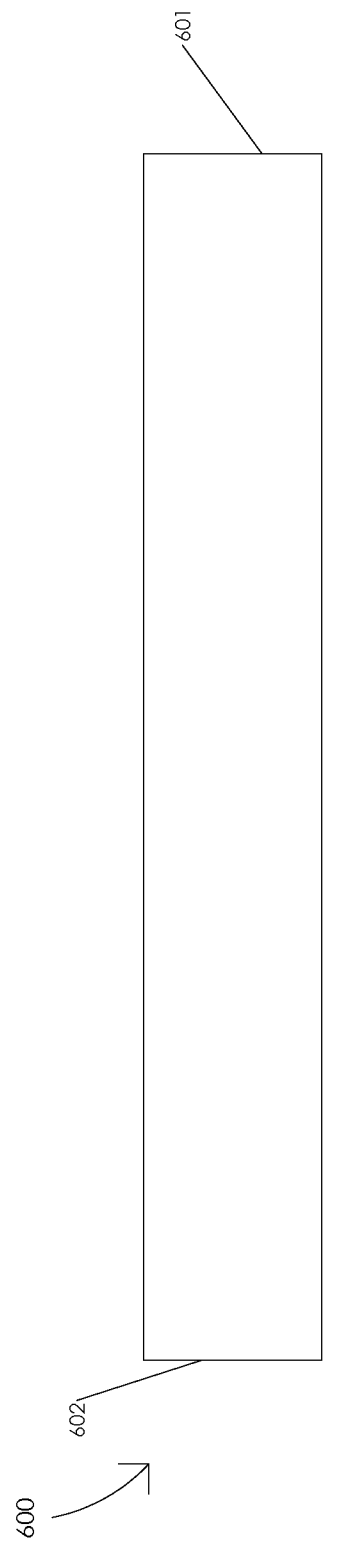
FIGS. 6A and 6B are schematic diagrams illustrating a handle facilitating sleeve.
Figure 6B:
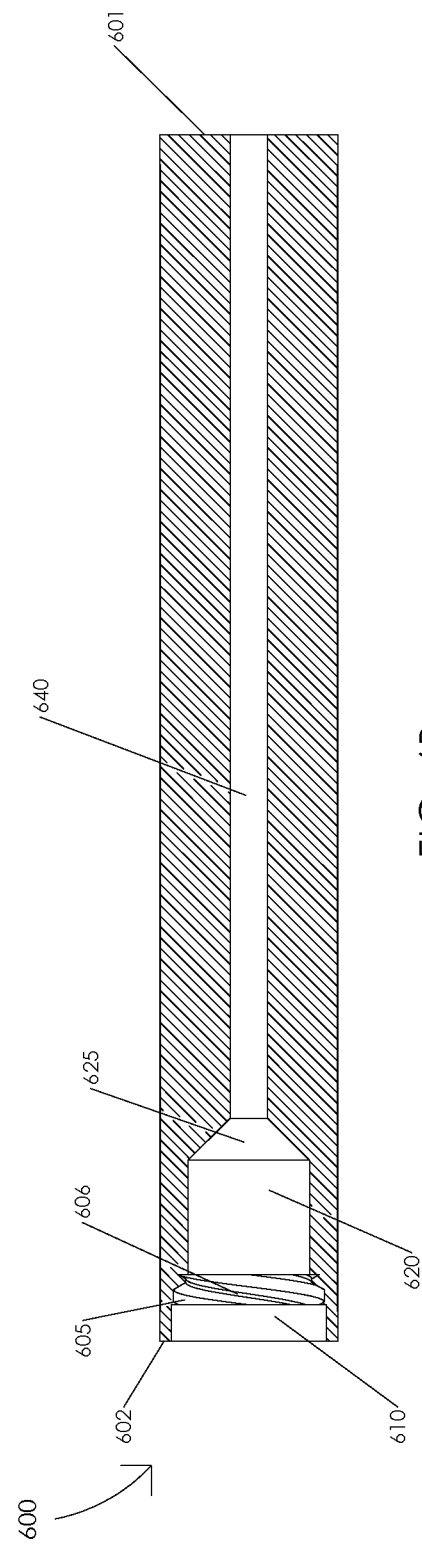

FIGS. 6A and 6B are schematic diagrams illustrating a handle facilitating sleeve 600. FIG. 6A illustrates a side view of a handle facilitating sleeve 600. FIG. 6B illustrates a cross-sectional view in a sagittal plane of a handle facilitating sleeve 600. In one or more embodiments, handle facilitating sleeve 600 may comprise a handle facilitating sleeve distal end 601 and a handle facilitating sleeve proximal end 602. Illustratively, handle facilitating sleeve 600 may be manufactured from a material configured to minimize a coefficient of friction between a portion of optic fiber 210 and a portion of handle facilitating sleeve 600, e.g., handle facilitating sleeve 600 may be manufactured from a self-lubricating thermoplastic material. In one or more embodiments, handle facilitating sleeve 600 may be manufactured from a material wherein a coefficient of friction between a portion of optic fiber 210 and a portion of handle facilitating sleeve 600 is in a range of 0.011 to 0.36, e.g., handle facilitating sleeve 600 may be manufactured from a material wherein a coefficient of friction between a portion of optic fiber 210 and a portion of handle facilitating sleeve 600 is 0.0311. Illustratively, handle facilitating sleeve 600 may be manufactured from a material wherein a coefficient of friction between a portion of optic fiber 210 and a portion of handle facilitating sleeve 600 is less than 0.011 or greater than 0.36. In one or more embodiments, handle facilitating sleeve 600 may be manufactured from a fluorocarbon material, e.g., handle facilitating sleeve 600 may be manufactured from a polytetrafluoroethylene material. Illustratively, handle facilitating sleeve 600 may be manufactured from an acetal-based polytetrafluoroethylene material, e.g., handle facilitating sleeve 600 may be manufactured from a turcite material. In one or more embodiments, handle facilitating sleeve 600 may be manufactured from a material having a density in a range of 0.024 to 0.073 pounds per cubic inch, e.g., handle facilitating sleeve 600 may be manufactured from a material having a density of 0.053 pounds per cubic inch. Illustratively, handle facilitating sleeve 600 may be manufactured from a material having a density of less than 0.024 pounds per cubic inch or greater than 0.073 pounds per cubic inch. In one or more embodiments, handle facilitating sleeve 600 may be manufactured from a material having a hardness in a range of 50 Shore D to 75 Shore D, e.g., handle facilitating sleeve 600 may be manufactured from a material having a hardness of 61 Shore D. Illustratively, handle facilitating sleeve 600 may be manufactured from a material having a hardness of less than 50 Shore D or greater than 75 Shore D. In one or more embodiments, optic fiber 210 may be manufactured from a material having a first hardness and handle facilitating sleeve 600 may be manufactured from a material having a second hardness. Illustratively, the first hardness may be greater than the second hardness. In one or more embodiments, optic fiber 210 may be manufactured from a material having a first hardness, handle facilitating sleeve 600 may be manufactured from a material having a second hardness, and transitory connector 100 may be manufactured from a material having a third hardness. Illustratively, the first hardness may be greater than the second hardness and the second hardness may be greater than the third hardness. In one or more embodiments, handle facilitating sleeve 600 may comprise a major diameter housing 605, a minor diameter housing 606, a second transitory connector housing 620, a second transitory connector housing proximal chamber 610, a second transitory connector housing distal taper 625, and a handle facilitating sleeve inner bore 640. Illustratively, second transitory connector housing distal taper 625 may be disposed between handle facilitating sleeve inner bore 640 and second transitory connector housing 620. In one or more embodiments, major diameter housing 605 may be disposed between second transitory connector housing proximal chamber 610 and second transitory connector housing 620. Illustratively, minor diameter housing 606 may be disposed between second transitory connector housing proximal chamber 610 and second transitory connector housing 620.

FIGS. 7A, 7B, 7C, 7D, 7E, and 7F are schematic diagrams illustrating a curved hypodermic tube. FIG. 7A illustrates a side view and a cross-sectional view in a sagittal plane of a first curved hypodermic tube 700. Illustratively, first curved hypodermic tube 700 may comprise a first curved hypodermic tube distal end 701 and a first curved hypodermic tube proximal end 702. In one or more embodiments, first curved hypodermic tube 700 may comprise a straight segment with medial termination 703, a single continuously non-tapered inner diameter 704, and a first curved portion 705. Illustratively, first curved hypodermic tube 700 may be manufactured by centerless grinding, e.g., a continuous tapered outer diameter of first curved hypodermic tube 700 may be manufactured by removing material from an outer diameter of first curved hypodermic tube 700 to fabricate a continuous taper. In one or more embodiments, a continuous tapered outer diameter of first curved hypodermic tube 700 may begin at an interface between straight segment with medial termination 703 and first curved portion 705 and continue to first curved hypodermic tube distal end 701. For example, first curved hypodermic tube 700 may have a first outer diameter at first curved hypodermic tube proximal end 702. Illustratively, first curved hypodermic tube 700 may have a second outer diameter at first curved hypodermic tube distal end 701. In one or more embodiments, the first outer diameter may be greater than the second outer diameter. Illustratively, first curved hypodermic tube 700 may have an outer diameter in a range of 0.0150 to 0.0226 inches at first curved hypodermic tube proximal end 702, e.g., first curved hypodermic tube 700 may have an outer diameter of 0.0179 inches at first curved hypodermic tube proximal end 702. In one or more embodiments, first curved hypodermic tube 700 may have an outer diameter of less than 0.0150 inches or greater than 0.0226 inches at first curved hypodermic tube proximal end 702. Illustratively, first curved hypodermic tube 700 may have an outer diameter in a range of 0.00893 to 0.0201 inches at first curved hypodermic tube distal end 701, e.g., first curved hypodermic tube 700 may have an outer diameter of 0.0142 inches at first curved hypodermic tube distal end 701. In one or more embodiments, first curved hypodermic tube 700 may have an outer diameter of less than 0.00893 inches or greater than 0.0201 inches at first curved hypodermic tube distal end 701. Illustratively, a line tangent to first curved hypodermic tube distal end 701 may intersect a line tangent to first curved hypodermic tube proximal end 702 at an angle in a range of 20.0 to 60.0 degrees, e.g., a line tangent to first curved hypodermic tube distal end 701 may intersect a line tangent to first curved hypodermic tube proximal end 702 at an angle of 46.83 degrees. In one or more embodiments, a line tangent to first curved hypodermic tube distal end 701 may intersect a line tangent to first curved hypodermic tube proximal end 702 at an angle of less than 20.0 degrees or greater than 60.0 degrees.

FIG. 7B illustrates a side view and a cross-sectional view in a sagittal plane of a second curved hypodermic tube 710. Illustratively, second curved hypodermic tube 710 may comprise a second curved hypodermic tube distal end 711 and a second curved hypodermic tube proximal end 712. In one or more embodiments, second curved hypodermic tube 710 may comprise a straight tube with medial termination 713, a single non-tapered tube with medial commencement 719, and a second curved portion 715. Illustratively, second curved hypodermic tube 710 may comprise an outer diameter tapered step 717, e.g., second curved hypodermic tube 710 may comprise an outer diameter tapered step 717 disposed between straight tube with medial termination 713 and single non-tapered tube with medial commencement 719. In one or more embodiments, straight tube with medial termination 713 may comprise a straight tube with medial termination inner diameter 714. Illustratively, single non-tapered tube with medial commencement 719 may comprise a single non-tapered tube with medial commencement inner diameter 716. In one or more embodiments, second curved hypodermic tube 710 may comprise an inner diameter tapered step 718, e.g., second curved hypodermic tube 710 may comprise an inner diameter tapered step 718 disposed between straight tube with medial termination inner diameter 714 and single non-tapered tube with medial commencement inner diameter 716. Illustratively, straight tube with medial termination 713 may have a first outer diameter and single non-tapered tube with medial commencement 719 may have a second outer diameter. In one or more embodiments, the first outer diameter may be greater than the second outer diameter. Illustratively, straight tube with medial termination 713 may have an outer diameter in a range of 0.0159 to 0.0201 inches, e.g., straight tube with medial termination 713 may have an outer diameter of 0.0179 inches. In one or more embodiments, straight tube with medial termination 713 may have an outer diameter of less than 0.0159 inches or greater than 0.0201 inches. Illustratively, single non-tapered tube with medial commencement 719 may have an outer diameter in a range of 0.0126 to 0.0159 inches, e.g., single non-tapered tube with medial commencement 719 may have an outer diameter of 0.0142 inches. In one or more embodiments, single non-tapered tube with medial commencement 719 may have an outer diameter of less than 0.0126 inches or greater than 0.0159 inches. Illustratively, a line tangent to second curved hypodermic tube distal end 711 may intersect a line tangent to second curved hypodermic tube proximal end 712 at an angle in a range of 20.0 to 60.0 degrees, e.g., a line tangent to second curved hypodermic tube distal end 711 may intersect a line tangent to second curved hypodermic tube proximal end 712 at an angle of 46.83 degrees. In one or more embodiments, a line tangent to second curved hypodermic tube distal end 711 may intersect a line tangent to second curved hypodermic tube proximal end 712 at an angle of less than 20.0 degrees or greater than 60.0 degrees.

FIG. 7C illustrates a side view and a cross-sectional view in a sagittal plane of a third curved hypodermic tube 720. Illustratively, third curved hypodermic tube 720 may s comprise a third curved hypodermic tube distal end 721 and a third curved hypodermic tube proximal end 722. In one or more embodiments, third curved hypodermic tube 720 may comprise a straight segment with medial termination 723, a non-tapered segment with medial commencement 729, and a third curved portion 725. Illustratively, third curved hypodermic tube 720 may comprise an outer diameter tapered step 727. In one or more embodiments, third curved hypodermic tube 720 may comprise a third curved hypodermic tube inner diameter 724, e.g., straight segment with medial termination 723 and non-tapered segment with medial commencement 729 may have a common inner diameter.

FIG. 7D illustrates a side view and a cross-sectional view in a sagittal plane of a fourth curved hypodermic tube 730. Illustratively, fourth curved hypodermic tube 730 may comprise a fourth curved hypodermic tube distal end 731 and a fourth curved hypodermic tube proximal end 732. In one or more embodiments, fourth curved hypodermic tube 730 may comprise a straight segment with distal termination 733, a non-tapered segment with distal commencement 739, and a fourth curved portion 735. Illustratively, fourth curved hypodermic tube 730 may comprise a fourth curved hypodermic tube inner diameter 734. In one or more embodiments, fourth curved hypodermic tube 730 may comprise an outer diameter tapered step 737, e.g., fourth curved hypodermic tube 730 may comprise an outer diameter tapered step 737 disposed between straight segment with distal termination 733 and non-tapered segment with distal commencement 739. Illustratively, a line tangent to fourth curved hypodermic tube distal end 731 may intersect a line tangent to fourth curved hypodermic tube proximal end 732 at an angle in a range of 20.0 to 50.0 degrees, e.g., a line tangent to fourth curved hypodermic tube distal end 731 may intersect a line tangent to fourth curved hypodermic tube proximal end 732 at an angle of 40.0 degrees. In one or more embodiments, a line tangent to fourth curved hypodermic tube distal end 731 may intersect a line tangent to fourth curved hypodermic tube proximal end 732 at an angle of less than 20.0 degrees or greater than 50.0 degrees.

FIG. 7E illustrates a side view and a cross-sectional view in a sagittal plane of a fifth curved hypodermic tube 740. Illustratively, fifth curved hypodermic tube 740 may comprise a fifth curved hypodermic tube distal end 741 and a fifth curved hypodermic tube proximal end 742. In one or more embodiments, fifth curved hypodermic tube 740 may comprise a straight segment with proximal termination 743, a medial tapered segment 747, a curved segment with distal commencement 749, and a fifth curved portion 745. Illustratively, medial tapered segment 747 may be disposed between straight segment with proximal termination 743 and curved segment with distal commencement 749. In one or more embodiments, fifth curved hypodermic tube 740 may comprise a fifth curved hypodermic tube inner diameter 744. Illustratively, a line tangent to fifth curved hypodermic tube distal end 741 may intersect a line tangent to fifth curved hypodermic tube proximal end 742 at an angle in a range of 10.0 to 40.0 degrees, e.g., a line tangent to fifth curved hypodermic tube distal end 741 may intersect a line tangent to fifth curved hypodermic tube proximal end 742 at an angle of 20.0 degrees. In one or more embodiments, a line tangent to fifth curved hypodermic tube distal end 741 may intersect a line tangent to fifth curved hypodermic tube proximal end 742 at an angle of less than 10.0 degrees or greater than 40.0 degrees.

FIG. 7F illustrates a side view and a cross-sectional view in a sagittal plane of a sixth curved hypodermic tube 750. Illustratively, sixth curved hypodermic tube 750 may comprise a sixth curved hypodermic tube distal end 751 and a sixth curved hypodermic tube proximal end 752. In one or more embodiments, sixth curved hypodermic tube 750 may comprise a straight segment with proximal termination 753, a medial curved segment 757, a distal curved segment 759, and a sixth curved portion 755. Illustratively, straight segment with proximal termination 753 may comprise a straight segment with proximal termination inner diameter 754. In one or more embodiments, medial curved segment 757 may comprise a medial curved segment inner diameter 758. Illustratively, distal curved segment 759 may comprise a distal curved segment inner diameter 760. Illustratively, a line tangent to sixth curved hypodermic tube distal end 751 may intersect a line tangent to sixth curved hypodermic tube proximal end 752 at an angle in a range of 20.0 to 60.0 degrees, e.g., a line tangent to sixth curved hypodermic tube distal end 751 may intersect a line tangent to sixth curved hypodermic tube proximal end 752 at an angle of 46.83 degrees. In one or more embodiments, a line tangent to sixth curved hypodermic tube distal end 751 may intersect a line tangent to sixth curved hypodermic tube proximal end 752 at an angle of less than 20.0 degrees or greater than 60.0 degrees.

Figure 8A:
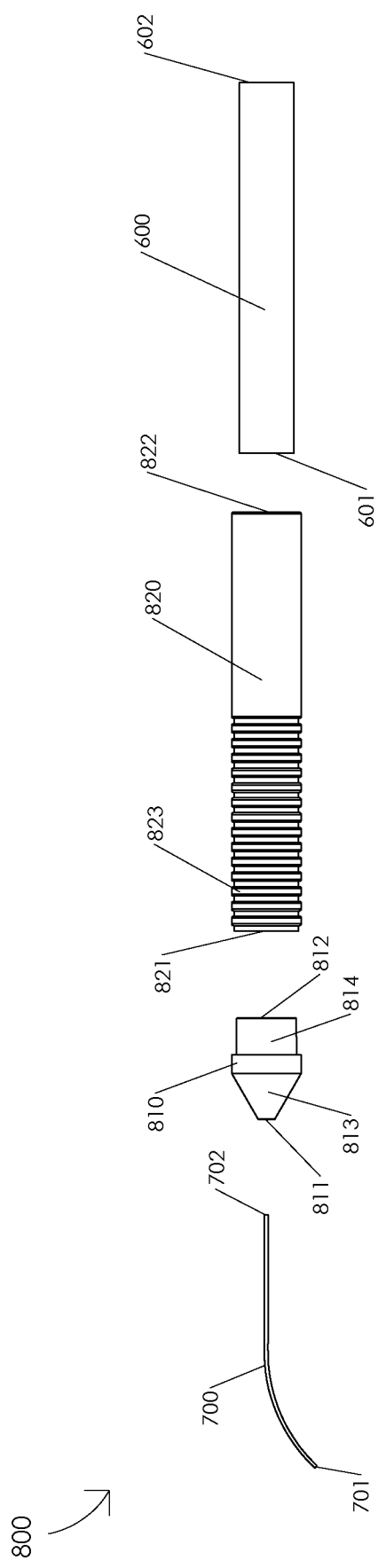
FIGS. 8A and 8B are schematic diagrams illustrating an exploded view of a reusable handle assembly.
Figure 8B:
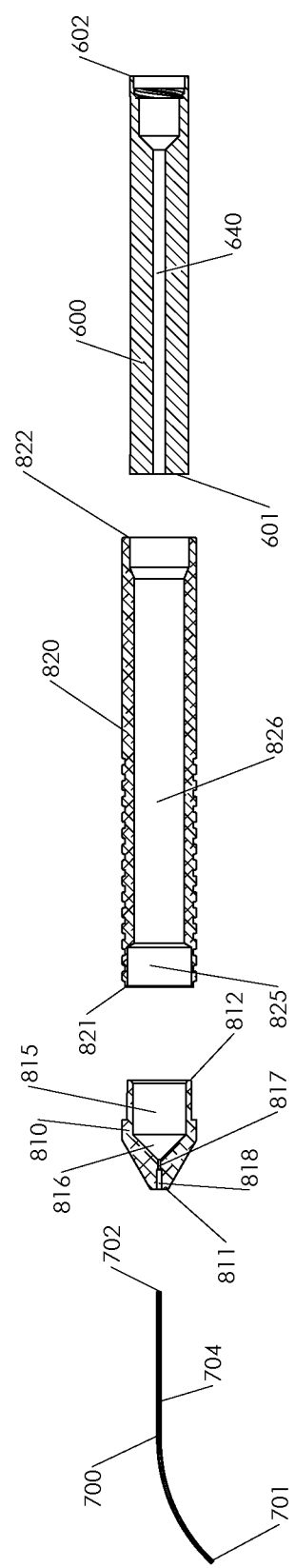

FIGS. 8A and 8B are schematic diagrams illustrating an exploded view of a reusable handle assembly 800. FIG. 8A illustrates a side view of a reusable handle assembly 800. FIG. 8B illustrates a cross-sectional view in a sagittal plane of a reusable handle assembly 800. In one or more embodiments, a reusable handle assembly 800 may comprise a first curved hypodermic tube 700, a handle nosecone 810, a handle base 820, and a handle facilitating sleeve 600. Illustratively, a reusable handle assembly 800 may comprise a second curved hypodermic tube 710. In one or more embodiments, a reusable handle assembly 800 may comprise a third curved hypodermic tube 720. Illustratively, a reusable handle assembly 800 may comprise a fourth curved hypodermic tube 730. In one or more embodiments, a reusable handle assembly 800 may comprise a fifth curved hypodermic tube 740. Illustratively, a reusable handle assembly 800 may comprise a sixth curved hypodermic tube 750. Illustratively, handle nosecone 810 may comprise a handle nosecone distal end 811 and a handle nosecone proximal end 812. In one or more embodiments, handle nosecone 810 may comprise a handle nosecone tapered portion 813 and a handle nosecone base 814. Illustratively, handle nosecone 810 may comprise a handle nosecone inner bore 815, a handle nosecone distal taper 816, an optic fiber distal end guide 817, and a hypodermic tube housing 818. In one or more embodiments, handle base 820 may comprise a handle base distal end 821 and a handle base proximal end 822. Illustratively, handle base 820 may comprise a grip portion 823. In one or more embodiments, handle base 820 may comprise a nosecone housing 825 and a handle facilitating sleeve housing 826.

FIGS. 9A and 9B are schematic diagrams illustrating an assembled reusable handle 900. FIG. 9A illustrates a side view of an assembled reusable handle 900. FIG. 9B illustrates a cross-sectional view in a sagittal plane of an assembled reusable handle 900. Illustratively, handle facilitating sleeve 600 may be disposed in a portion of handle base 820, e.g., handle facilitating sleeve 600 may be disposed in handle facilitating sleeve housing 826. In one or more embodiments, handle facilitating sleeve 600 may be disposed in a portion of handle base 820 wherein handle facilitating sleeve proximal end 602 is adjacent to handle base proximal end 822, e.g., handle facilitating sleeve 600 may be disposed in a portion of handle base 820 wherein handle facilitating sleeve proximal end 602 abuts handle base proximal end 822. Illustratively, handle facilitating sleeve 600 may be fixed in a portion of handle base 820, e.g., handle facilitating sleeve 600 may be fixed in a portion of handle base 820 by an adhesive, an epoxy, a crimp, a weld, a friction fit, etc. In one or more embodiments, handle facilitating sleeve 600 may be fixed in handle facilitating sleeve housing 826, e.g., handle facilitating sleeve 600 may be fixed in handle facilitating sleeve housing 826 by an adhesive, an epoxy, a crimp, a weld, a friction fit, etc.

Illustratively, a portion of handle nosecone 810 may be disposed in a portion of handle base 820, e.g., handle nosecone proximal end 812 may be disposed in nosecone housing 825. In one or more embodiments, handle nosecone base 814 may be disposed in a portion of handle base 820, e.g., handle nosecone base 814 may be disposed in a portion of handle base 820 wherein handle nosecone distal end 811 extends out from handle base distal end 821. Illustratively, a portion of handle nosecone 810 may be disposed in a portion of handle base 820 wherein handle nosecone proximal end 812 is adjacent to handle facilitating sleeve distal end 601, e.g., a portion of handle nosecone 810 may be disposed in a portion of handle base 820 wherein handle nosecone proximal end 812 abuts handle facilitating sleeve distal end 601. In one or more embodiments, a portion of handle nosecone 810 may be fixed in a portion of handle base 820, e.g., a portion of handle nosecone 810 may be fixed in a portion of handle base 820 by an adhesive, an epoxy, a crimp, a weld, a friction fit, etc. Illustratively, a portion of handle nosecone 810 may be fixed in handle nosecone housing 825, e.g., a portion of handle nosecone 810 may be fixed in handle nosecone housing 825 by an adhesive, an epoxy, a crimp, a weld, a friction fit, etc.

In one or more embodiments, a portion of first curved hypodermic tube 700 may be disposed in a portion of handle nosecone 810, e.g., first curved hypodermic tube proximal end 702 may be disposed in hypodermic tube housing 818. Illustratively, a portion of first curved hypodermic tube 700 may be disposed in a portion of handle nosecone 810 wherein first curved hypodermic tube distal end 701 extends out from handle nosecone distal end 811. In one or more embodiments, a portion of first curved hypodermic tube 700 may be fixed in a portion of handle nosecone 810, e.g., a portion of first curved hypodermic tube 700 may be fixed in a portion of handle nosecone 810 by an adhesive, an epoxy, a crimp, a weld, a friction fit, etc. Illustratively, a portion of first curved hypodermic tube 700 may be fixed in hypodermic tube housing 818, e.g., a portion of first curved hypodermic tube 700 may be fixed in hypodermic tube housing 818 by an adhesive, an epoxy, a crimp, a weld, a friction fit, etc.

Figure 10A:
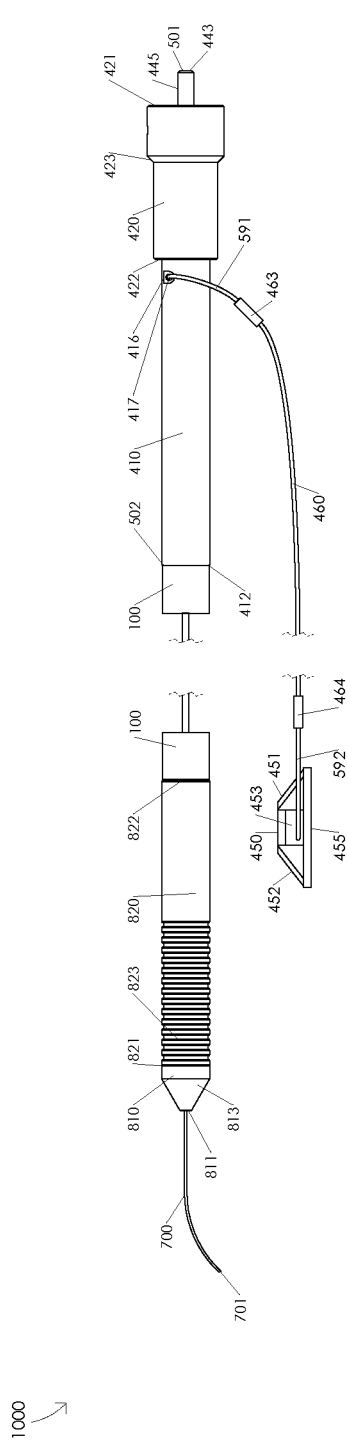
FIGS. 10A and 10B are schematic diagrams illustrating an assembled curved laser probe with single-use optic fiber.
Figure 10B:
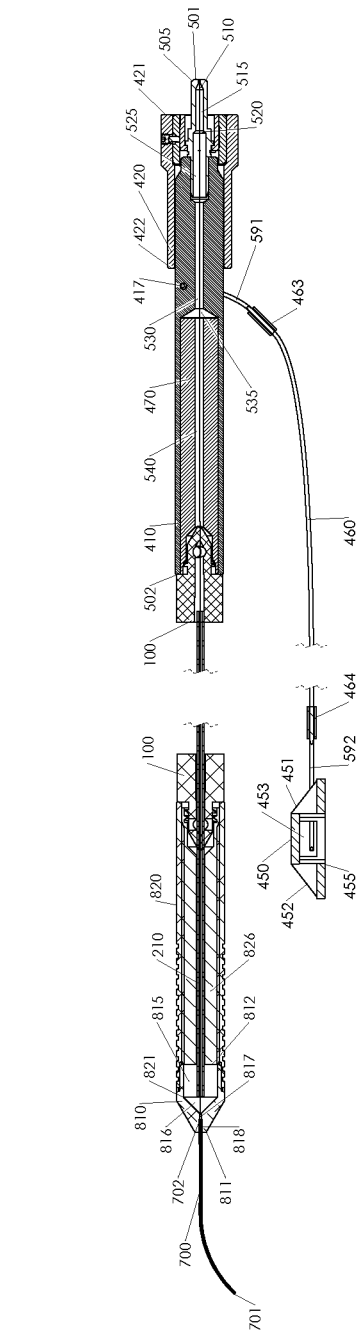

FIGS. 10A and 10B are schematic diagrams illustrating an assembled curved laser probe with single-use optic fiber 1000. FIG. 10A illustrates a side view of an assembled curved laser probe with single-use optic fiber 1000. FIG. 10B illustrates a cross-sectional view in a sagittal plane of an assembled curved laser probe with single-use optic fiber 1000. Illustratively, an assembled curved laser probe with single-use optic fiber 1000 may comprise an assembled single-use optic fiber 300, an assembled optic fiber fixture 500, and an assembled reusable handle 900. In one or more embodiments, an assembled curved laser probe with single-use optic fiber 1000 may comprise a first transitory connector 100 disposed in a portion of assembled optic fiber fixture 500 and a second transitory connector 100 disposed in apportion of assembled reusable handle 900.

In one or more embodiments, an assembled curved laser probe with single-use optic fiber 1000 may comprise a first transitory connector 100 disposed in a portion of assembled optic fiber fixture 500 wherein optic fiber proximal end 212 is adjacent to assembled optic fiber fixture distal end 501. Illustratively, an assembled curved laser probe with single-use optic fiber 1000 may comprise a first transitory connector 100 disposed in a portion of assembled optic fiber fixture 500 wherein optic fiber proximal end 212 abuts assembled optic fiber fixture distal end 501. In one or more embodiments, an assembled curved laser probe with single-use optic fiber 1000 may comprise a first transitory connector 100 disposed in a portion of assembled optic fiber fixture 500 wherein optic fiber proximal end 212 is coplanar with assembled optic fiber fixture distal end 501. Illustratively, inserting a portion of optic fiber 210 into a portion of assembled optic fiber fixture 500 may be configured to ingress optic fiber proximal end 212 into first transitory connector housing 550. In one or more embodiments, inserting a portion of optic fiber 210 into a portion of assembled optic fiber fixture 500 may be configured to ingress optic fiber proximal end 212 into first transitory connector housing distal taper 545. Illustratively, first transitory connector housing distal taper 545 may be configured to guide an ingress of optic fiber 210 into fixture facilitating sleeve inner bore 540. In one or more embodiments, inserting a portion of optic fiber 210 into a portion of assembled optic fiber fixture 500 may be configured to ingress optic fiber proximal end 212 into fixture facilitating sleeve inner bore 540. Illustratively, inserting a portion of optic fiber 210 into a portion of assembled optic fiber fixture 500 may be configured to ingress optic fiber proximal end 212 into fixture facilitating sleeve housing 535. In one or more embodiments, fixture facilitating sleeve housing 535 may be configured to guide an ingress of optic fiber 210 into fixture base inner bore 530. Illustratively, inserting a portion of optic fiber 210 into a portion of assembled optic fiber fixture 500 may be configured to ingress optic fiber proximal end 212 into fixture base inner bore 530. In one or more embodiments, inserting a portion of optic fiber 210 into a portion of assembled optic fiber fixture 500 may be configured to ingress optic fiber proximal end 212 into machine connector proximal taper 444. Illustratively, machine connector proximal taper 444 may be configured to guide an ingress of optic fiber 210 into machine connector proximal inner lumen 525. In one or more embodiments, inserting a portion of optic fiber 210 into a portion of assembled optic fiber fixture 500 may be configured to ingress optic fiber proximal end 212 into machine connector proximal inner lumen 525. Illustratively, inserting a portion of optic fiber 210 into a portion of assembled optic fiber fixture 500 may be configured to ingress optic fiber proximal end 212 into inner lumen proximal taper 520. In one or more embodiments, inner lumen proximal taper 520 may be configured to guide an ingress of optic fiber into machine connector distal inner lumen 515. Illustratively, inserting a portion of optic fiber 210 into a portion of assembled optic fiber fixture 500 may be configured to ingress optic fiber proximal end 212 into machine connector distal inner lumen 515. In one or more embodiments, inserting a portion of optic fiber 210 into a portion of assembled optic fiber fixture 500 may be configured to ingress optic fiber proximal end 212 into inner lumen distal taper 510. Illustratively, inner lumen distal taper 510 may be configured to guide an ingress of optic fiber 210 into optic fiber proximal end guide 505. In one or more embodiments, inserting a portion of optic fiber 210 into a portion of assembled optic fiber fixture 500 may be configured to ingress optic fiber proximal end 212 into optic fiber proximal end guide 505.

Illustratively, inserting first transitory connector 100 into a portion of assembled optic fiber fixture 500 may be configured to ingress optic fiber 210 into optic fiber proximal end guide 505, e.g., inserting first transitory connector 100 into a portion of assembled optic fiber fixture 500 may be configured to ingress optic fiber 210 into optic fiber proximal end guide 505 wherein optic fiber proximal end 212 is coplanar with assembled optic fiber fixture distal end 501. In one or more embodiments, inserting first transitory connector distal end 101 into first transitory connector housing distal taper 545 may be configured to ingress optic fiber 210 into optic fiber proximal end guide 505, e.g., inserting first transitory connector distal end 101 into first transitory connector housing distal taper 545 may be configured to ingress optic fiber 210 into optic fiber proximal end guide 505 wherein optic fiber proximal end 212 is coplanar with assembled optic fiber fixture distal end 501. Illustratively, inserting first transitory connector nosecone base 120 into first transitory connector housing 550 may be configured to ingress optic fiber 210 into optic fiber proximal end guide 505, e.g., inserting first transitory connector nosecone base 120 into first transitory connector housing 550 may be configured to ingress optic fiber 210 into optic fiber proximal end guide 505 wherein optic fiber proximal end 212 is coplanar with assembled optic fiber fixture distal end 501. In one or more embodiments, inserting major diameter 105 and minor diameter 106 into first transitory connector housing threading 560 may be configured to ingress optic fiber 210 into optic fiber proximal end guide 505, e.g., inserting major diameter 105 and minor diameter 106 into first transitory connector housing threading 560 may be configured to ingress optic fiber 210 into optic fiber proximal end guide 505 wherein optic fiber proximal end 212 is coplanar with assembled optic fiber fixture distal end 501. Illustratively, rotating major diameter 105 and minor diameter 106 in first transitory connector housing threading 560 may be configured to ingress optic fiber 210 into optic fiber proximal end guide 505, e.g., rotating major diameter 105 and minor diameter 106 in first transitory connector housing threading 560 may be configured to ingress optic fiber 210 into optic fiber proximal end guide 505 wherein optic fiber proximal end 212 is coplanar with assembled optic fiber fixture distal end 501. In one or more embodiments, rotating major diameter 105 and minor diameter 106 in first transitory connector housing threading 560 may be configured to fix first transitory connector 100 in assembled optic fiber fixture 500, e.g., rotating major diameter 105 and minor diameter 106 in first transitory connector housing threading 560 may be configured to fix major diameter 105 and minor diameter 106 in first transitory connector housing threading 560. For example, major diameter 105 and minor diameter 106 may comprise a threaded fastener.

Illustratively, inserting a portion of optic fiber 210 into a portion of assembled reusable handle 900 may be configured to ingress optic fiber distal end 211 into second transitory connector housing 620. In one or more embodiments, inserting a portion of optic fiber 210 into a portion of assembled reusable handle 900 may be configured to ingress optic fiber distal end 211 into second transitory connector housing distal taper 625. Illustratively, second transitory connector housing distal taper 625 may be configured to guide an ingress of optic fiber 210 into handle facilitating sleeve inner bore 640. In one or more embodiments, inserting a portion of optic fiber 210 into a portion of assembled reusable handle 900 may be configured to ingress optic fiber distal end 211 into handle facilitating sleeve inner bore 640. Illustratively, inserting a portion of optic fiber 210 into a portion of assembled reusable handle 900 may be configured to ingress optic fiber distal end 211 into handle nosecone inner bore 815. In one or more embodiments, inserting a portion of optic fiber 210 into a portion of assembled reusable handle 900 may be configured to ingress optic fiber distal end 211 into handle nosecone distal taper 816. Illustratively, handle nosecone distal taper 816 may be configured to guide an ingress of optic fiber 210 into optic fiber distal end guide 817. In one or more embodiments, inserting a portion of optic fiber 210 into a portion of assembled reusable handle 900 may be configured to ingress optic fiber distal end 211 into optic fiber distal end guide 817. Illustratively, inserting a portion of optic fiber 210 into a portion of assembled reusable handle 900 may be configured to ingress optic fiber distal end 211 into a curved hypodermic tube.

Illustratively, inserting second transitory connector 100 into a portion of assembled reusable handle 900 may be configured to ingress optic fiber 210 into a curved hypodermic tube, e.g., inserting second transitory connector 100 into a portion of assembled reusable handle 900 may be configured to ingress optic fiber 210 into a curved hypodermic tube wherein optic fiber distal end 211 is adjacent to a curved hypodermic tube distal end. In one or more embodiments, inserting second transitory connector 100 into a portion of assembled reusable handle 900 may be configured to ingress optic fiber 210 into a curved hypodermic tube wherein optic fiber distal end 211 is coplanar with a curved hypodermic tube distal end. Illustratively, inserting second transitory connector distal end 101 into second transitory connector housing distal taper 625 may be configured to ingress optic fiber 210 into a curved hypodermic tube, e.g., inserting second transitory connector distal end 101 into second transitory connector housing distal taper 625 may be configured to ingress optic fiber 210 into a curved hypodermic tube wherein optic fiber distal end 211 is adjacent to a curved hypodermic tube distal end. In one or more embodiments, inserting second transitory connector distal end 101 into second transitory connector housing distal taper 625 may be configured to ingress optic fiber 210 into a curved hypodermic tube wherein optic fiber distal end 211 is coplanar with a curved hypodermic tube distal end. Illustratively, inserting second transitory connector nosecone base 120 into second transitory connector housing 620 may be configured to ingress optic fiber 210 into a curved hypodermic tube, e.g., inserting second transitory connector nosecone base 120 into second transitory connector housing 620 may be configured to ingress optic fiber 210 into a curved hypodermic tube wherein optic fiber distal end 211 is adjacent to a curved hypodermic tube distal end. In one or more embodiments, inserting second transitory connector nosecone base 120 into second transitory connector housing 620 may be configured to ingress optic fiber 210 into a curved hypodermic tube wherein optic fiber distal end 211 is coplanar with a curved hypodermic tube distal end. Illustratively, inserting major diameter 105 in major diameter housing 605 may be configured to ingress optic fiber 210 into a curved hypodermic tube, e.g., inserting major diameter 105 in major diameter housing 605 may be configured to ingress optic fiber 210 into a curved hypodermic tube wherein optic fiber distal end 211 is adjacent to a curved hypodermic tube distal end. In one or more embodiments, inserting major diameter 105 in major diameter housing 605 may be configured to ingress optic fiber 210 into a curved hypodermic tube wherein optic fiber distal end 211 is coplanar with a curved hypodermic tube distal end. Illustratively, inserting minor diameter 106 into minor diameter housing 606 may be configured to ingress optic fiber 210 into a curved hypodermic tube, e.g., inserting minor diameter 106 into minor diameter housing 606 may be configured to ingress optic fiber 210 into a curved hypodermic tube wherein optic fiber distal end 211 is adjacent to a curved hypodermic tube distal end. In one or more embodiments, inserting minor diameter 106 into minor diameter housing 606 may be configured to ingress optic fiber 210 into a curved hypodermic tube wherein optic fiber distal end 211 is coplanar with a curved hypodermic tube distal end. Illustratively, rotating major diameter 105 in major diameter housing 605 may be configured to ingress optic fiber 210 into a curved hypodermic tube, e.g., rotating major diameter 105 in major diameter housing 605 may be configured to ingress optic fiber 210 into a curved hypodermic tube wherein optic fiber distal end 211 is adjacent to a curved hypodermic tube distal end. In one or more embodiments, rotating major diameter 105 in major diameter housing 605 may be configured to ingress optic fiber 210 into a curved hypodermic tube wherein optic fiber distal end 211 is coplanar with a curved hypodermic tube distal end. Illustratively, rotating minor diameter 106 in minor diameter housing 606 may be configured to ingress optic fiber 210 into a curved hypodermic tube, e.g., rotating minor diameter 106 in minor diameter housing 606 may be configured to ingress optic fiber 210 into a curved hypodermic tube wherein optic fiber distal end 211 is adjacent to a curved hypodermic tube distal end. In one or more embodiments, rotating minor diameter 106 in minor diameter housing 606 may be configured to ingress optic fiber 210 into a curved hypodermic tube wherein optic fiber distal end 211 is coplanar with a curved hypodermic tube distal end.

Illustratively, rotating major diameter 105 in major diameter housing 605 may be configured to fix second transitory connector 100 in assembled reusable handle 900, e.g., rotating major diameter 105 in major diameter housing 605 may be configured to fix major diameter 105 in major diameter housing 605. In one or more embodiments, rotating minor diameter 106 in minor diameter housing 606 may be configured to fix second transitory connector 100 in assembled reusable handle 900, e.g., rotating minor diameter 106 in minor diameter housing 606 may be configured to fix minor diameter 106 in minor diameter housing 606. For example, major diameter 105 and minor diameter 106 may comprise a threaded fastener. Illustratively, a user may perform a photocoagulation procedure with an assembled curved laser probe with single-use optic fiber 1000. In one or more embodiments, a user may connect machine connector 440 to a laser machine. Illustratively, a user may energize the laser machine to deliver laser light into optic fiber proximal end 212, through optic fiber 210, out from optic fiber distal end 211, and onto a surgical target site. In one or more embodiments, assembled reusable handle 900 may be a reusable medical device sold non-sterile and sterilized by a user in a medical autoclave.

The foregoing description has been directed to particular embodiments of this invention. It will be apparent; however, that other variations and modifications may be made to the described embodiments, with the attainment of some or all of their advantages. Specifically, it should be noted that the principles of the present invention may be implemented in any system. Furthermore, while this description has been written in terms of a laser probe, the teachings of the present invention are equally suitable to any systems where the functionality may be employed. Therefore, it is the object of the appended claims to cover all such variations and modifications as come within the true spirit and scope of the invention.

What is claimed is:

1. An instrument comprising:
   a first transitory connector having a first transitory connector distal end and a first transitory connector proximal end;
   a first inner bore of the first transitory connector;
   a first inner bore distal taper of the first transitory connector;
   a first optic fiber housing of the first transitory connector;
   a second transitory connector having a second transitory connector distal end and a second transitory connector proximal end;
   a second inner bore of the second transitory connector;
   a second inner bore distal taper of the second transitory connector;
   a second optic fiber housing of the second transitory connector;
   a jacketing having a jacketing distal end and a jacketing proximal end wherein the jacketing distal end is disposed in the first inner bore and wherein the jacketing proximal end is disposed in the second inner bore;
   a curved hypodermic tube having a curved hypodermic tube distal end and a curved hypodermic tube proximal end;
   an optic fiber having an optic fiber distal end and an optic fiber proximal end, the optic fiber disposed in the jacketing, the first inner bore, the first inner bore distal taper, the first optic fiber housing, the second inner bore, the second inner bore distal taper, and the second optic fiber housing wherein a first portion of the optic fiber is fixed in the first optic fiber housing and a second portion of the optic fiber is fixed in the second optic fiber housing and wherein the optic fiber distal end extends a first distance from the first transitory connector distal end and the optic fiber proximal end extends a second distance from the second transitory connector proximal end and wherein the first distance is equal to the second distance;
   a handle facilitating sleeve having a handle facilitating sleeve distal end and a handle facilitating sleeve proximal end;
   a transitory connector housing of the handle facilitating sleeve;
   a handle facilitating sleeve inner bore of the handle facilitating sleeve; and
   wherein the handle facilitating sleeve is manufactured from a material having a first hardness and the optic fiber is manufactured from a material having a second hardness wherein the second hardness is greater than the first hardness.

2. The instrument of claim 1 further comprising:
   a major diameter of the first transitory connector.

3. The instrument of claim 2 further comprising:
   a minor diameter of the first transitory connector.

4. The instrument of claim 1 wherein the handle facilitating sleeve and the optic fiber have a coefficient of friction in a range of 0.011 to 0.36.

5. The instrument of claim 1 wherein the handle facilitating sleeve and the optic fiber have a coefficient of friction of less than 0.011.

6. The instrument of claim 1 wherein the handle facilitating sleeve is manufactured from a fluorocarbon material.

7. The instrument of claim 1 wherein the handle facilitating sleeve is manufactured from a material having a density in a range of 0.024 to 0.073 pounds per cubic inch.

8. The instrument of claim 1 wherein the handle facilitating sleeve is manufactured from a self-lubricating thermoplastic material.

9. The instrument of claim 1 wherein the handle facilitating sleeve is manufactured from a TURCITE material.

10. The instrument of claim 1 wherein the handle facilitating sleeve is manufactured from a material having a hardness in a range of 50 Shore D to 75 Shore D.

11. The instrument of claim 1 further comprising:
    a handle base having a handle base distal end and a handle base proximal end; and
    a handle facilitating sleeve housing of the handle base.

12. The instrument of claim 11 wherein the handle facilitating sleeve is disposed in the handle facilitating sleeve housing.

13. The instrument of claim 12 further comprising:
    a handle nosecone having a handle nosecone distal end and a handle nosecone proximal end; and
    a hypodermic tube housing of the handle nosecone.

14. The instrument of claim 13 further comprising:
a nosecone housing of the handle base wherein the handle nosecone is disposed in the nosecone housing.

15. The instrument of claim 1 wherein the curved hypodermic tube is manufactured by centerless grinding.

16. The instrument of claim 1 further comprising:
a continuous taper of an outer diameter of the curved hypodermic tube.

17. The instrument of claim 1 further comprising:
a single continuously non-tapered inner diameter of the curved hypodermic tube.

18. The instrument of claim 1 further comprising:
a straight segment with medial termination of the curved hypodermic tube.

\* \* \* \* \*